United States Patent [19]

Subramanian et al.

[11] Patent Number: 5,223,219
[45] Date of Patent: Jun. 29, 1993

[54] ANALYTICAL CARTRIDGE AND SYSTEM FOR DETECTING ANALYTES IN LIQUID SAMPLES

[75] Inventors: Kumar Subramanian, Alameda, Calif.; Jeffrey Sugarman, Sunnyvale; Bernhard B. Sterling, Danville; Fred Voss, Pleasanton; Marina Saltman, Redwood City, all of Calif.

[73] Assignee: Biotrack, Inc., Mountain View, Calif.

[21] Appl. No.: 867,162

[22] Filed: Apr. 10, 1992

[51] Int. Cl.$^5$ .............. G01N 11/04; B01L 11/00
[52] U.S. Cl. .............. 422/55; 422/52; 422/82; 422/82.09; 422/73; 422/102; 422/119; 210/451; 210/505
[58] Field of Search .............. 422/55, 58, 82.09, 73, 422/102, 119, 82; 210/451, 505

[56] References Cited

U.S. PATENT DOCUMENTS

| | | |
|---|---|---|
| 3,799,742 | 3/1974 | Coleman . |
| 4,233,029 | 11/1980 | Columbus . |
| 4,426,451 | 1/1984 | Columbus . |
| 4,618,476 | 10/1986 | Columbus ............ 422/100 |
| 4,637,403 | 1/1987 | Garcia et al. ............ 128/770 |
| 4,753,776 | 6/1988 | Hillman et al. ............ 422/101 |
| 4,756,884 | 7/1988 | Hillman et al. ............ 422/73 |
| 4,820,491 | 4/1990 | Khoja et al. ............ 422/63 |
| 4,820,647 | 4/1989 | Gibbons ............ 436/79 |
| 4,829,011 | 5/1989 | Gibbons ............ 436/512 |
| 4,868,129 | 9/1989 | Gibbons et al. ............ 436/179 |
| 4,946,795 | 8/1990 | Gibbons et al. ............ 436/179 |
| 4,952,373 | 8/1990 | Sugarman et al. ............ 422/99 |
| 5,004,923 | 4/1991 | Hillman et al. ............ 250/341 |
| 5,039,617 | 8/1991 | McDonald et al. ............ 436/69 |
| 5,077,017 | 12/1991 | Gorin et al. ............ 422/100 |

Primary Examiner—James C. Housel
Assistant Examiner—N. Bhat
Attorney, Agent, or Firm—Cooley Godward Castro Huddleson & Tatum

[57] ABSTRACT

A diagnosis system, which comprises a monitor, comprising a detector providing multiple reflectance readings in an array of individual locations, registering an analytical cartridge in the monitor at a fixed location and orientation relative to the array, and determines and displays analytical results from reflectance readings; and an analytical cartridge, comprising a liquid impervious housing, a sample application site in the housing located outside the monitor when the cartridge is registered in the monitor by the means for registering, one or more reflectance reading sites in the housing that register with one or more of the locations in the array, a capillary pathway in the housing leading from the sample application site to each of the reflectance reading sites, and a reflectance matrix located in at least one of the reflectance reading sites. In some embodiments of the invention, control features that optimize accuracy of measurement by controlling when and if sample reaches reflectance reading sites and by drawing excess sample away from undesirable locations in the cartridge are present. One control element balances the liquid-holding capacities of the application site, the sample-transporting capillary passageway that leads to the reflectance reading site, and the porous matrices from which the reflectance reading will be made, so that excess sample is excluded from entry into the cartridge while sample volumes that are below the minimum necessary for accurate operation do not reach the matrix, thereby avoiding false readings.

34 Claims, 8 Drawing Sheets

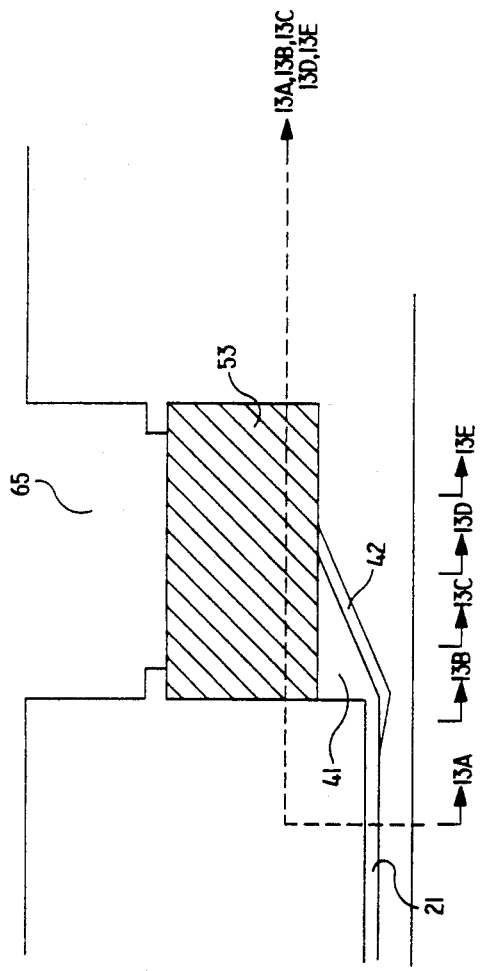
FIG. 12
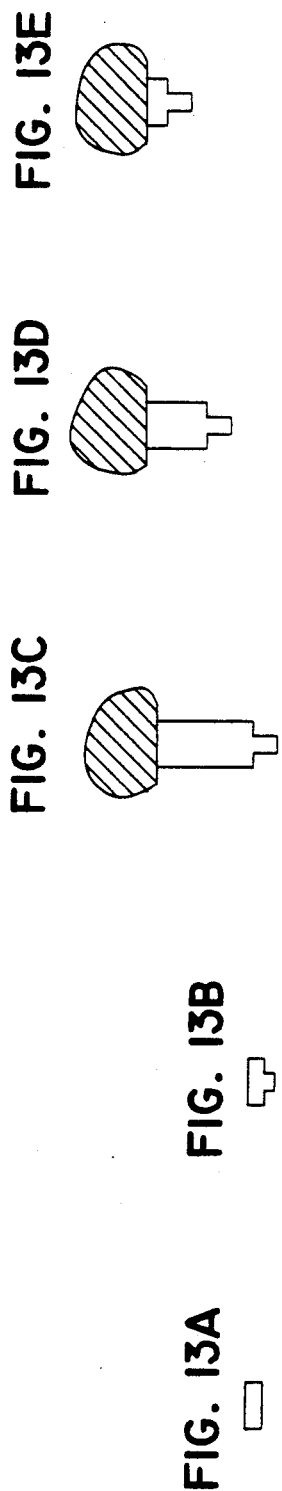
FIG. 13A
FIG. 13B
FIG. 13C
FIG. 13D
FIG. 13E
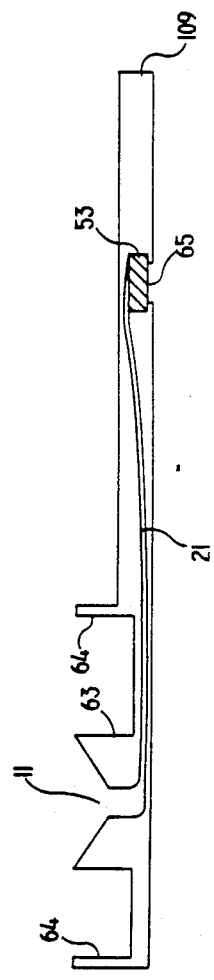
FIG. 14

ANALYTICAL CARTRIDGE AND SYSTEM FOR DETECTING ANALYTES IN LIQUID SAMPLES

INTRODUCTION

1. Technical Field

This invention is directed to analytical systems and is particularly directed to small, patient-side analytical systems that can conduct a chemical or biochemical analysis on a sample of body fluid, such as blood.

2. Background

A wide variety of assays have been developed that involve reaction of a sample with reagents present in a porous substrate. In some of these operations, sample is applied to a porous strip at the same location where reagent is present. Reaction takes place at that location, and the assay results are either determined visually or by reflectance spectrophotometry after insertion of the test strip into an appropriate reading device. In other cases, liquid sample migrates through a porous medium to react at a second location, with the results being obtained as above.

However, such assays have a number of difficulties when they are being used by an untrained operator or by a patient's bedside at a location remote from a testing laboratory. Quantitative determination of results is difficult when test strips are visually inspected. Although accurate readings can be taken in a reflectance spectrophotometer, the test strip must be inserted into a spectrophotometer and the operation of the spectrophotometer must be properly carried out, which is difficult for untrained users. Similar problems exist for strips which transport sample by absorption into a porous strip, but such strips also require greater amounts of sample to wet the entire length of a porous strip.

Any analytical system that is used patient-side needs to operate in the simplest possible manner. For example, a user should not be required to activate switches, close or open light-tight doors, or manipulate the sample or the reagent strip or other material to which the sample has been added after addition of the sample. Such manipulations decrease the accuracy of the assay results when required of an untrained user. Additionally, any assay system that uses blood as the sample should use the minimum volume possible because of the difficulties in obtaining blood samples from patients, particularly if the sample is being obtained by the patient herself. When patients obtain their own blood samples, capillary blood obtained by a finger stick is preferred because of the ease of operation, but only small volumes (less than 50 $\mu$l) will be available for assays.

Some of these constraints are contradictory. Application of a small drop of blood or other sample to a test strip and analysis at the same location generally requires manipulation of the test strip or monitor in some fashion, such as by closing a light-tight door in order to prevent ambient light from interfering with reflectance readings. Sample transport systems have generally required larger amounts of sample and have therefore not been applied to small, single-drop samples.

U.S. Pat. No. 4,756,844, assigned to the same assignee as the present invention, describes methods and devices using unitary capillary flow tracks to draw samples applied to a disposable cartridge into the interior of a monitor using capillary action. Examples of such analytical systems include the Biotrack PT and PTT systems, which measure rates of blood clotting. Further development of such systems to allow simultaneous determination of several analytes and to extend the measurement capacity to different kinds of analytes is clearly desirable.

3. Relevant Literature

A number of devices exist for determining analytes in small volumes of sample using disposable cartridges and table-top analytical instruments. U.S. Pat. No. 4,756,884 describes methods and devices using capillary flow tracks for analyzing samples for the presence of analytes or for the properties of the samples, such as clotting rates of blood samples. Analytical cartridges capable of carrying out more than one type of analysis in a single disposable cartridge are described in U.S. patent application Ser. No. 348,519, filed May 8, 1989 and now abandoned. U.S. Pat. No. 4,233,029 describes a liquid transport device formed by opposed surfaces spaced apart a distance effective to provide capillary flow of liquid without providing any means to control the rate of capillary flow. U.S. Pat. Nos. 4,618,476 and 4,233,029 describe a similar capillary transport device having speed and meniscus control means. U.S. Pat. No. 4,426,451 describes another similar capillary transport device including means for stopping flow between two zones, flow being resumed by the application of an externally generated pressure. U.S. Pat. No. 3,799,742 describes an apparatus in which a change in surface character from hydrophilic to hydrophobic is used to stop flow of a small sample, thereby metering the sample present. U.S. Pat. Nos. 4,946,795 and 5,077,017 describe a number of dilution and mixing cartridges in which mixing takes place in small capillary and non-capillary spaces.

SUMMARY OF THE INVENTION

It is an object of the present invention to provide an analytical cartridge that is adaptable for use with a variety of different analyses in a single monitor, with the cartridge being one of several similar cartridges capable of being used with the same monitor.

It is a further object of the invention to provide a disposable cartridge that will draw a small drop of applied sample entirely into the interior of the cartridge and thus into the interior of a monitor into which the cartridge is inserted without requiring additional manipulation by the user.

It is still another object of the invention to provide fail-safe operation regardless of the sample volume applied to a cartridge of the invention.

It is still another object of the invention to provide a cartridge that can be used with any of the currently existing or future-developed solid substrate assays that rely on reflectance readings from a reflective matrix while still retaining the advantages of the invention described herein.

These and other objects of the invention have been accomplished by providing a diagnosis system which comprises a monitor and an analytical cartridge that is insertable into the monitor. The monitor contains multiple light sources and detectors for taking reflectance readings in an array of individual locations in the cartridge when it is present in the interior of the monitor. The cartridge is positively held in a fixed location so that reflectance reading sites in the cartridge are oriented properly relative to the reflectance reading devices. While the number of reflectance reading devices in the monitor is fixed, the number of reflectance reading sites in the analytical cartridge can vary with the needs of the individual cartridge. When the analytical cartridge is inserted in the monitor, a portion of the analytical cartridge extends outside the housing of the monitor so that sample can be applied to the analytical cartridge. One (or more than one) capillary pathway connects the application site to each of the reflectance reading sites. The analytical cartridge can be one member of a collection of cartridges, each of which differs in some aspect of the chemistry present on the reflective matrices present at the reflective reading sites, and each of which further can have different reflectance reading sites as long as the reading sites are located in the proper orientation relative to the array of reflectance reading devices present in the monitor. Various embodiments of the invention can also include functional features designed to optimize accuracy of measurement, such as by controlling when and if sample reaches reflectance reading sites and by drawing excess sample away from undesirable locations in the cartridge. For example, by balancing the liquid-holding capacities of the application site, the sample-transporting capillary passageway that leads to the reflectance reading site, and the porous matrices from which the reflectance reading will be made, excess sample can be excluded from entry into the cartridge while sample volumes that are below the minimum necessary for accurate operation do not reach the matrix, thereby avoiding false readings.

BRIEF DESCRIPTION OF THE DRAWINGS

The invention now being generally described, the same will be better understood by reference to the following detailed description of the invention when considered in combination with the drawings that form part of the specification, wherein:

FIGS. 10–13A, 13B, 13C, 13D and 13E are views embodiments for controlling entry of sample into an assay stack.

FIG. 14 is a cross-sectional view of a ninth embodiment of a cartridge of the invention.

DESCRIPTION OF SPECIFIC EMBODIMENTS

Figure 1A:
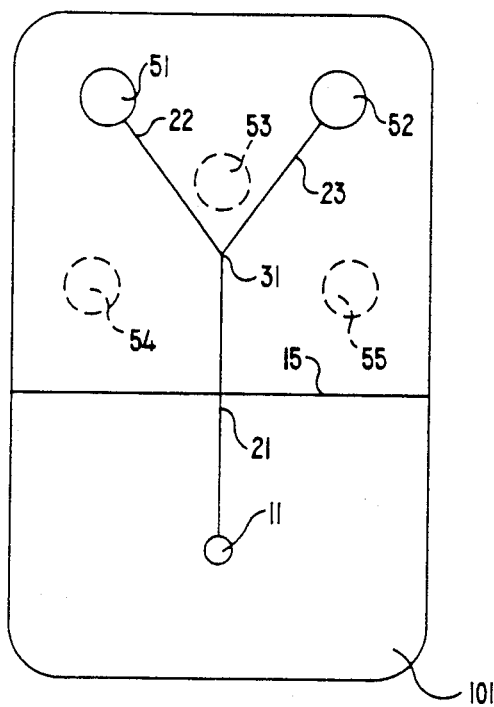
FIG. 1A, 1B, 1C, 1D are plan views of four cartridges of the invention in which an application site and a series of branching capillaries direct sample to any of five potential individual reflectance reading sites.
Figure 1B:
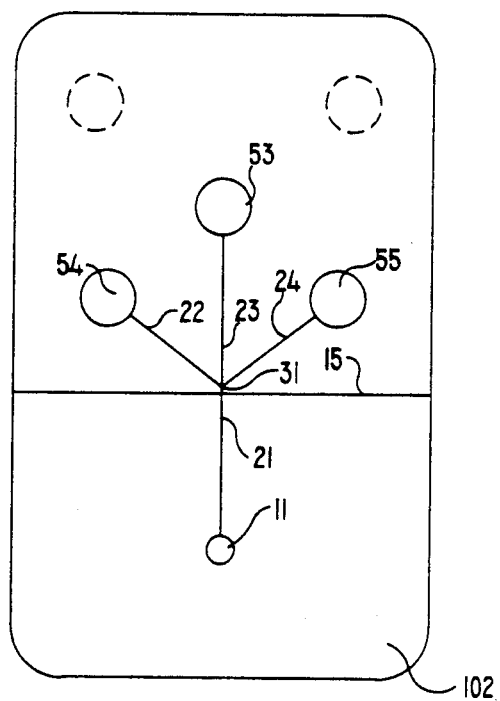
Figure 1C:
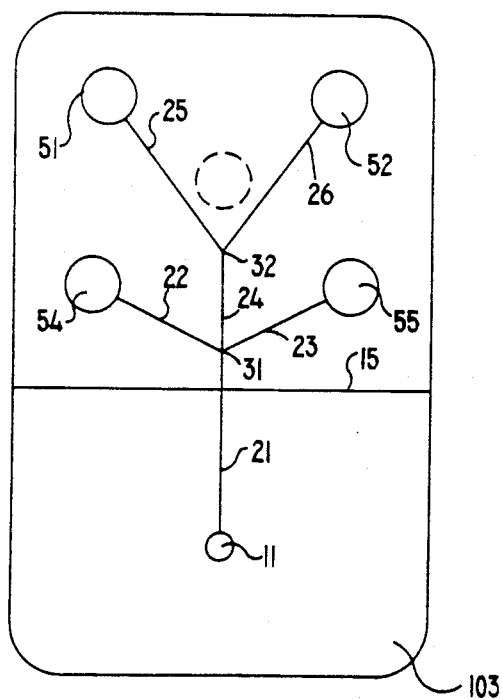
Figure 1D:
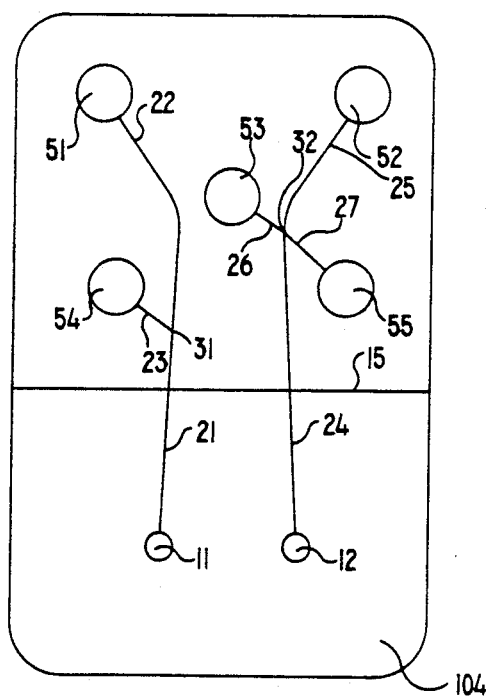

The present invention comprises a system that assays sets of analytes (or in some cases single analytes) in small samples of blood or other sample fluids. The system comprises (1) disposable cartridges containing mechanical and chemical means to (a) process (move, aliquot, mix, remove red cells, etc.) and (b) react with specific analytes in a fluid sample, usually whole blood, and (2) a monitor, which is a small electro-mechanical device that can register the disposable cartridge, regulates its temperature, determine reflectance of a set of assay locations, and calculate the assay results, among other functions.

Cartridges/monitor systems for different sets of analytes are possible (e.g., glucose, cholesterol, hemoglobin; total cholesterol, HDL-cholesterol, triglyceride). Each system will have a different cartridge, and the physical layout and construction of each cartridge can be different. All cartridges in a set, however, will have identical exterior dimensions and will have reflective matrices located at one or more locations of a set of fixed locations. The monitor will be common to all assays in a set.

Typically, the chemistry in a given assay converts the analyte to a colored product (chromophore). This product changes the reflectance of a diffusely reflective membrane that is measured by the monitor at a wavelength corresponding to an appropriate, usually the maximum, absorbance of the chromophore.

The monitor is equipped with light sources, usually one or more light-emitting-diodes (LEDs). For example, four diodes with emissions that cover the visible and near infrared (IR) part of the electromagnetic spectrum can be used. The visible and IR LEDs cover a broad wavelength range, which allows for measurement of a large variety of color-forming chemistries, especially those that generate a colored product by oxidation of a leucodye by hydrogen peroxide catalyzed by peroxidase.

In one preferred version of the monitor, light from the LEDs is mixed and routed from the sources to the stacks using a fiber optic. In this way all of the stacks can be illuminated by all the light sources. By operating the sources in a timed sequence and multiplexing the response from the reflectance detectors, it is possible to measure reflectance at all illuminating wavelengths at all the stacks over the assay time courses.

The disposable analytical cartridges will comprise a liquid impervious housing, a sample application site, a reflectance reading site that will be located in the monitor when the cartridge is inserted into the monitor, a sample-transporting capillary passageway connecting the application site to the reflectance reading site, and a porous matrix located in the reflectance reading site. Liquid-holding capacities of the sample application site, the sample-transporting capillary passageway, and the porous matrix will be selected so that the sample-transport capacity is greater than the porous-matrix capacity and the application-site capacity is less than the sum of the sample-transport capacity and porous-matrix capacity. By providing these relative capacities, and by selecting the capillary transport properties of the various passageways and components to selectively draw sample toward the porous matrix sample, using the design requirements discussed in detail below, very small samples can be drawn entirely into the porous matrix so that no sample is wasted in either the application site or the sample-transporting capillary passageway. On the other hand, proper design of the application site and use of additional capillary passageways to control excess sample allow proper operation of the cartridge in the hands of an unskilled user.

Overview of System and Its Operation

This initial description is of a typical version of a cartridge and is intended to provide an overview. The key component parts of the invention are discussed later in detail with their function.

Each cartridge comprises a housing made of injection molded plastic (for example acrylonitrile/butadiene/styrene or "ABS") containing other physical and chemical components to be described later. Preparation of similar cartridges for other purposes is described in the previously cited patents and applications. To perform an assay, an operator inserts the cartridge into the monitor, which is activated by the insertion. The cartridge generally has graphics, registering holes, and slots so that insertion can only be achieved in the correct orientation. The cartridge is basically flat (with some projections as noted below) and is typically operated in the horizontal orientation, although other orientations are permitted. A bar code (or other signal) on the cartridge identifies the cartridge and its expiry date and is readable by the monitor, which has recognition optics or other sensory devices. If the monitor recognizes the cartridge and the expiry date has not elapsed, the monitor displays a set of instructions for the user; if not, an error message is displayed. Before the user is prompted to apply a sample, the cartridge is heated to a fixed temperature, if required by an assay on the cartridge. On prompting, the user applies a drop of blood to an application port which is located on the upper side of the part of the cartridge that projects from the monitor. This port is usually surrounded by a land that is in turn surrounded at its edge by a small lip (see FIG. 3 and its discussion). The land and lip serve to prevent any sample that overflows the application port from reaching the monitor or its surroundings. Sample flows from the application port into a capillary channel enclosed in the cartridge, the driving force being largely capillary. Unbalanced gravitational forces are usually also present during early stages of sample movement, but are typically not present or relatively small after sample fully enters the horizontal sample-transport capillary. The interior surfaces of the plastic of which the cartridge is made are modified (if necessary) by an etching process to render the interior capillary passageways hydrophilic so that the blood will spread spontaneously over the pathway surfaces by capillary force. Sample moves through the capillary until it reaches one or more junctions to other branching channels that lead to a set of assay stacks, each of which is a porous matrix or a series of porous matrices in close contact with each other. Different layers of the assay stack can provide for different functions, such as filtering of red cells from blood, separating reagents from each other, or acting as a reflective matrix of which an optical reading is taken. Such assay stacks are conventional, as discussed below. The stacks are captured in a (usually circular) interior chamber or external cavity in the cartridge. In preferred embodiments, channels molded into the base of the stack cavity where the capillary channel joins the cavity to aid in directing the sample to flow uniformly into the stack. The stack itself is composed of a series of (generally) disc-shaped, porous components disposed co-axially with the cavity axis and captured in the cavity in preferred embodiments by a ledge in the outer surface of the cartridge projecting from the cavity wall towards the center. In such embodiments there is a hole in the cartridge exposing a diffusely reflective membrane both to the atmosphere and to the optics of the monitor. In other embodiments, the stacks are completely enclosed in an internal chamber, and reflectance readings are taken through the housing material, which is transparent to the wavelength of radiation being used, at least in the location of the chamber through which the reading takes place. The stack components are closely apposed to form a structure which has continuous capillarity such that the sample is drawn into the stack until, eventually, the pores are saturated. In cartridges with more than one stack, all the stacks fill with sample, provided sufficient sample has been applied. The order and rate of filling is determined by the dimensions of capillary channels and the structure of the stacks, as discussed below. In general however, all the stacks can easily be designed to fill within less than three minutes.

In tests where plasma is the desired sample and whole blood is the sample, the stack acts as a red cell filter. Filter stacks comprise a fibrous layer (typically polypropylene) containing a red cell agglutinating agent dried onto the fibrous material. As the sample moves through the filter, the agent dissolves in the plasma and causes red cells to agglutinate and thus to become trapped within the fibrous filter. Plasma, now largely free of red cells, proceeds through the stack. A thin membrane layer can be placed next to the fibrous layer to remove any remaining red cells if more stringent separation is required than is available by use of the filter alone. Plasma then moves into a layer impregnated with assay chemistry which dissolves in the plasma and reacts with the analyte to form a colored product. Assay chemistry will typically include salts, buffers, detergents, enzymes, chromogens, stabilizing agents, and bactericides or bacteriostats. Usually the layer that carries the assay chemistry is the outermost layer of the stack. The outer layer, which functions as a reflective matrix, and the chromogen are carefully selected such that in the range of clinical interest the layer is optically thick and the reflectivity of the layer after the assay reaction corresponds to K/S values in the range 0.2-2. A layer is optically thick when increases in the thickness of the layer have no effect on reflectance readings regardless of the material present on the side of a layer away from the incident light. An example of such selection is discussed in detail below. Optionally, the fibrous layer can contain assay chemistry, buffers, salts, surface active agents, or stabilizing reagents. Other porous layers may be present to carry ancillary reagents, control fluid motions, to reflect or absorbs light, or for other purposes.

The monitor records the reflectance of the carrier layer during the assay reaction, typically at three wavelengths. By comparing the change in reflectance with those for known calibration materials, the monitor can compute the analyte concentration. The second and third wavelengths can be used for quality control operations and for other purposes. The monitor can also determine if operation of the device has been compromised or if the sample has been damaged (for example hemolyzed), since these conditions produce characteristic reflectance values.

In some assays, for example that of hemoglobin, where the required sample is whole blood, a porous, reagent-containing disc is substituted for the red cell filter. By appropriate choice of porosity and reagent formulation, a uniform mixture of blood and reagent forms in the disc and can then be subjected to optical analysis.

In assaying several analytes, existing systems make undesirable compromises. Either assay performance (precision, accuracy) is not adequate for optimal patient care or the system configuration and assay protocol are cumbersome and elaborate and only suited for a laboratory setting. The present invention allows high quality assay performance to be combined with user convenience and system reliability. The following is a list of functional attributes of the invention and their structural corollaries.

1. A very small sample volume can be used. This is due to the small size of the stacks and to the ability of the system to use the entire sample to fill the stacks. The porosity of the stacks can be selected so that sample is drawn from the feeding capillaries entirely into the stacks. In other words, the sample application site and transport capillaries can be drained without compromising the results. Use of a molded housing (which is rigid) permits precise registration of the stacks with the optics in the monitor and well-defined, highly reproducible micro-cavities to accommodate the stacks.

2. Multiple results can be obtained from a single unmeasured sample drop. This is achieved by the capillary channels that connect a single application site to several stacks. To be able to get results from a single drop (typically about 35 uL), the small volume of the stacks and the capillary passageways leading to them is important. This feature represents a critical improvement over systems presently available.

3. Assays with very different chemical constraints (e.g., clinical range, type of analyte) can be determined in the same device at the same time. For example, different assays can have very different quantities of analyte to measure. Glucose is found in 1-25 mM concentrations in human blood plasma, whereas to measure the enzyme alanine aminotransferase in a reasonable time frame requires measurement of 0-0.2 mM enzyme product. To enable the measurement of analytes at such different levels using chemistry that converts the analyte stoichiometrically to light-absorbing products, it is advantageous to select optimal chromophores and reflective membranes which satisfy constraints for optimally precise and accurate determination of reflectance. The present invention allows for a wide variety of chromophores and reflective membranes such that an optimal selection can be made for a wide variety of analytes. An exemplary list of analytes and corresponding preferred chromophores and reflective membranes is provided in Table 1 below and illustrates techniques for modifying K/S values to accommodate different analyte concentrations.

TABLE 1

Pairing of Chromogens and Carriers with Kubelka-Munk (K/S) Requirements and Analyte Range in Blood

| Analyte Range (mM) | Analyte | Chromogen[5] | Carrier | K/S Range |
|---|---|---|---|---|
| 0-2.5 | HDL-Cholesterol | MAPS<br>TOOS<br>DAOS | Durapore<br>HT Tuffryn 450<br>Durapore | 0-2.5 |

TABLE 1-continued

| | | | | |
|---|---|---|---|---|
| 0-5 | Trig.[2] | TOOS<br>MBTH<br>DAOS | Supor 800<br>HT Tuffryn 450<br>Durapore | 0-1.8<br>0-1<br>0-4 |
| 0-15 | Chol.[3] | TOOS<br>MBTH<br>DAOS | HT Tuffryn 450<br>Durapore<br>HT Tuffryn 650 | 0-2.1<br>0-7<br>0-1.6 |
| 0-25 | Glu.[4] | MAOS<br>DAOS<br>MAOS | HT Tuffryn 450<br>HT Tuffryn 450<br>Supor 800 | 0-1.4<br>0-2<br>0-3 |

*Analyte range is based on peroxide/peroxidase system. Final carrier/chromogen selection requires consideration of other factors such as chemical yield.
*Acronyms are appended (Table 1 Appendix)
[1]HDL = High density lipoprotein
[2]Trig. = Triglyceride
[3]Chol. = Cholesterol
[4]Glu. = Glucose
[5]Chromogen is indicated compound plus amino anti-pyrine (AAP)

Appendix to Table 1

| Chromogen | Chemical Name |
|---|---|
| DAOS | N-ethyl-N-(2-hydroxy-3-sulfopropyl) 3,5-dimethoxyaniline Sodium Salt |
| MAOS | N-ethyl-N-(2-hydroxy-3-sulfopropyl) 3,5-dimethylaniline Sodium Salt |
| MAPS | N-ethyl-N-sulfopropyl-3,5-dimethyaniline Sodium Salt |
| TOOS | N-ethyl-N-(2-hydroxy-3-sulfopropy) m-Toluidine Sodium Salt |
| TMB | 3,3',5,5'-Tetramethylbenzidine |
| MBTH | 3-Methyl-2-benzothiazolinone hydrazone hydrochloride |
| HT Tuffryn series | polysulfone polymer |
| Supor series | polyethersulpone polymer |
| Durapor (GVWP) | polyvinylidene difluoride (fluoropolymer) |

4. Different configurations of tests are possible. In the basic version of the system that is described in detail below, 1-5 assays can be done; sample can be applied to one, two, or more application sites and one, two, or more tracks can be present in different cartridges. More complex assay can be carried out by expanding the number of the assay sites in the cartridge and/or adding, mixing or pretreatment chambers.

5. Blood sample hematocrit variation does not affect the results for analytes (such as glucose) where plasma concentration is the relevant analytical parameter. The assay stack absorbs an appropriate plasma sample based on its capacity, blood being drawn into the blood filter until saturation is achieved. Thus, samples that vary from 0 to 60% hematocrit (volume fraction of red cells) can be assayed without human intervention or compromise of assay results.

6. In assays for plasma analytes, fail-safe operation of the invention can be monitored with respect to leakage of red cells and hemolysis of sample by provision of a fail-safe stack which has no chemistry or by spectral analysis of the color of the assay stacks. The monitor can measure any red pigment (hemoglobin) which reaches the reflective membrane. The fail-safe stack is physically equivalent to the assay stacks in dimensions and in the construction of the red cell filter.

7. Timing of assays can be controlled by the disposition of stacks and dimensions of the capillaries serving them and by the structure of the stacks.

8. Pre-treatment can be provided, for example, by use of a mixing chamber containing a reagent: see application Ser. No. 07/867,155, entitled "Capillary Mixing Device," filed on even date with and assigned to the same assignee as the present invention.

Additional Description of Components Also Used in Prior Devices

A number of individual components used in the system of the present invention, such capillary tracks to transport and analyze liquid samples, have been developed in the laboratories of the assignee of the present inventors and are the subject of issued patents and other currently pending patent applications. Those components of the system that were previously known are described in sufficient detail below to enable one skilled in the art to practice the present invention. Background information and a number of additional details are set forth in the patents and patent applications that originally described these individual aspects of the system and which are incorporated into this specification by reference.

The analytical cartridge used in this invention is similar in its overall appearance and method of manufacture to previously described single-use, disposable, analytical cartridges developed in the laboratories of the present inventors, which are most often made by welding together two or more plastic pieces (usually prepared by injection molding) containing various channels and chambers. Sample movement is typically but not necessarily provided by capillary force; some gravitational forces are usually present, although they are generally small (but not the detailed discussion of avoiding unnecessary gravitational forces as described for preferred embodiments below). The cartridge can contain multiple chambers capable of mixing sample in multiple capillary tracks, multiple chambers in a single track, or only a single chamber in a single capillary track. The capillary tracks commonly comprise an entry port for entry of sample into the track, a capillary section that provides for sample flow and containment, and a vent to allow trapped air to escape so that capillary flow can take place. In some cases multiple capillary tracks use a common sample entry port; in other cases, entirely separate tracks with separate entry ports are provided.

The capillary sections are generally divided into several subsections that provide for different functions, such as sample flow, dissolution of reagent, analysis of results, verification of proper operation, or venting of air. The geometry of these sections vary with their purpose. For example, dissolution and/or mixing of reagents normally takes place in broad capillary chambers that provide a large surface area to which reagents can be applied and from which they will be rapidly re-suspended or dissolved upon contact by sample. Sample flow is normally regulated by the dimensions of the capillary channels and the physical properties of the sample intended for use in a given cartridge. Analysis and verification subsections of the capillary passageways and various chambers will have geometries shaped to cooperate with the detection system being used, such as flat or curved surfaces that cooperate with light passing through the walls of the capillary track so that the light is dispersed, concentrated, or left unaffected, depending on the desired result. For additional description of capillary flow devices with these elements, see U.S. Pat. No. 4,756,884, U.S. application Ser. Nos. 016,506, filed Feb. 17, 1987, and U.S. Pat. No. 5,039,617.

Liquids entering the cartridge can be modified in the capillary tracks or in an entry port prior to entry of sample into the capillary track to provide a sample better suited to a particular analysis. For example, blood can be filtered to provide plasma or lysed to provide a uniform, lysed medium. Filtration of red blood cells in capillary tracks is described in U.S. Pat. No. 4,753,776. The sample can also be lysed by passage through a porous disc, which contains an agent that lyses red cells (discussed in detail below). The "lysate" can then be distributed into one or more capillary tracks for the individual assays.

The assay system also comprises a monitor (analytical instrument) capable of reading at least one and usually more assays simultaneously. The monitor will therefore comprise detection systems and can also include verification systems (each of which can be a detection system utilized with different software or hardware in the detector or can be a separate system at various locations in the monitor) to detect any failure of the system. Monitors for performing single analyses are described in U.S. Pat. No. 4,756,884 and in U.S. application Ser. Nos. 016,506, filed Feb. 17, 1987, and 341,079, filed Apr. 20, 1989. Also, see U.S. Pat. No. 4,829,011 for a detector system that can be used in a monitor to detect agglutination of particles in a capillary track. These monitors can be readily adapted to use in the present invention simply by including the appropriate reflectance detectors, which can be adapted from known sources When used to detect the presence, absence, or amount of a particular analyte in a mixed sample, the monitor is provided with appropriate analysis and verification systems. For a number of systems that can be used to determine whether analysis has occurred correctly in a cartridge inserted into an instrument (and therefore not visible to the user), see U.S. application Ser. No. 337,286, filed Apr. 13, 1989.

Other monitor systems and a number of types of disposable cartridges that could be used for one or more analyses are disclosed in U.S. Pat. No. 4,756,884, which is assigned to the assignee of the present application. Other devices and techniques are described in U.S. Pat. Nos. 4,946,795, 5,077,017, and 4,820,647.

A number of operations of the cartridges refer to a "stop-flow junction." The phrase "stop-flow junction" refers to a control region in a capillary passageway that has been used in a number of prior inventions arising out of the laboratories of the inventors and in other laboratories (see, for example, U.S. Pat. Nos. 3,799,742 and 4,946,795). A stop-flow junction is a region in a fluid track that marks the junction between an early part of the track in which sample flows by capillary action (and optionally gravity) and a later part of the fluid track into which sample does not normally flow until flow is initiated by some outside force, such as an action of the user. For example, the stop-flow junction can be used to halt flow while a mixing operation takes place. A number of stop-flow junctions are described in U.S. Pat. Nos. 4,868,129 and 5,077,017 and in application Ser. Nos. 07/337,286, filed Apr. 13, 1989, and 07/663,217, filed Mar. 1, 1991.

DESCRIPTION OF SPECIFIC EMBODIMENTS WITH REFERENCES TO FIGURES

The general operation of the system of the invention can be understood by reference to the Figures, in which the same reference numbers used in different embodiments refer to features that perform the same function. However, the physical location of certain common features, such as capillary tracks and application sites, may be different from embodiment to embodiment.

FIG. 1 shows four different cartridges of the invention and how such cartridges can be utilized to direct sample to different members of an array of locations at which reflectance readings will be made. The cartridges shown in FIG. 1 (and throughout) are generally transparent or translucent. Thus the interior capillaries and chambers are visible through the exterior cartridge surface, as shown in the plan views of FIG. 1.

Cartridge 101 contains a single application site 11 and two assay stacks 51 and 52. The application site will be located outside the monitor when a cartridge is inserted in the monitor, while the assay stacks will be located inside the monitor. Dividing line 15 shows the extent to which the cartridge will be inserted into the monitor. Application site 11 in this embodiment is essentially a simple cavity opening in a surface of cartridge 101. Assay stacks 51 and 52 are vented to atmosphere in order to allow gases to escape (or access to atmosphere oxygen). The venting operation is not shown in this Figure but is shown in detail in other embodiments and Figures.

Capillary passageway 21 leads from application site 11 to branch point 31, at which point the capillary passageway divides into two passageways (22 and 23), each leading to one of the individual assay stacks. As will become evident by discussion of the remaining cartridges shown in FIG. 1, this cartridge is one member of a system in which there are five possible locations at which assay stacks can occur for a reflectance reading. The three unused locations are indicated by dashed circles with references numbers 53, 54, and 55. However, there are no specific features in cartridge 101 associated with these reference numbers, which are merely physical locations at which assay stacks will be located in other cartridges of the same system.

This is shown in cartridge 102, which is the same size and outward appearance as cartridge 101 and contains the same initial application site 11 and initial passageway 21. However, branch point 31 occurs at a different location and branch capillary passageways 22, 23, and 24 lead to assay stacks at locations 53, 54, and 55. In this embodiment assay stacks are not present at locations 51 and 52, and there is no feature of cartridge 102 associated with these locations.

Cartridge 103 is similar to cartridges 101 and 102 in that it contains a single application site 11 and a single initial capillary passageway 21. Here branch point 31 leads to three capillary passageways 22, 23, and 24. The first two of these lead to assay stacks 54 and 55, while the third leads to a second branching point 32 with capillaries 25 and 26 leading to assay stacks 51 and 52 respectively. In this cartridge no assay stack is present at location 55.

The final cartridge in the Figure, cartridge 104, utilizes all five of the assay stack locations. It also differs from the other cartridges of the same group in having two application sites. However, the exterior physical dimensions of this cartridge are the same, the location of the assay stacks are the same, and the cartridge can be used in the same monitor.

In cartridge 104, sample added to application site 11 is led by capillary passageway 21 to branch point 31 at which the sample divides and passes through capillary passageways 22 and 23 into assay stacks 51 and 54. A second sample added to application site 12 passes through capillary passageway 24 to branch point 32 where the sample divides and is carried by capillaries 25, 26, and 27 to assay stacks 52, 53, and 54.

Although FIG. 1 shows four different cartridges utilizing a specific array of five assay site locations, neither the number of assay site locations or the specific orientation of the locations in the array is required to be the same as that shown in this Figure. Other patterns and other numbers of assay stack locations can be used as long as the monitor is designed concurrently with the cartridge so that a reflectance reader is present at each location in which an assay stack can potentially be located.

Figure 2:
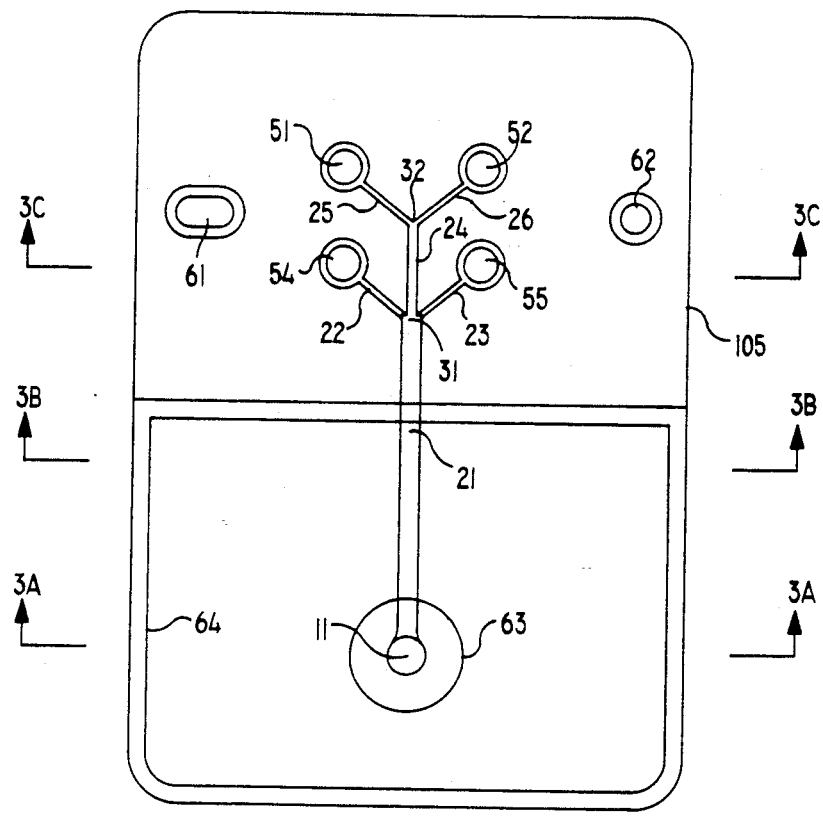
FIG. 2 is a plan view of a fifth embodiment of a cartridge of the invention.

FIG. 2 is a plan view of a cartridge that resembles cartridge 103 of FIG. 1 but which shows more details of the physical features of the cartridge associated with flow control aspects of the present invention. Here cartridge 105 has an application site 11, an initial capillary passageway 21, and an array of branching capillaries and assay stacks in the same pattern and with the same reference numbers shown in cartridge 103 of FIG. 1. Among the additional features that are visible in this Figure, it can be seen that the branching capillary passageways, generally referred to as a capillary tree, contain capillary passageways of different sizes. Initial capillary passageway 21 is the widest of the capillary passageways. (Generally, all capillary passageways will have the same height for ease of construction, although this can vary as discussed below.) At branch point 31, the two capillary passageways 22 and 23 leading to assay stacks 54 and 55 are smaller than passageway 24 leading to branch point 32. At branch point 32, two small capillaries 25 and 26 lead to assay stacks 51 and 52. By having the capillary passageways become smaller as they move further away from application site, the capillaries act to draw liquid forward along the capillary track. Smaller capillary passageways exert a greater force on the liquid so that sample is drawn with more force along such passageways. Thus, the ever smaller branching of the capillary passageways, combined with the small capillary passageways present in the porous material in the assay stacks (discussed in detail below), function to draw liquid sample applied at application site 11 fully into the reaction stacks. This allows reactions to be completed even if only barely enough sample is applied to fill all of the reaction stacks. Thus, assays can be carried out on smaller volumes of sample than are required for continuous porous materials, such as paper strips, which absorb large amounts of liquid at undesirable locations relative to the liquid that actually reaches the reaction location.

The cartridge is designed for close fit into a reflectance reading monitor and is thus provided with holes 61 and 62 which fit over corresponding pins in the monitor to properly register monitor optics and the reflectance reading sites in the cartridge. Other types of registration devices could likewise be used.

Figure 3C:
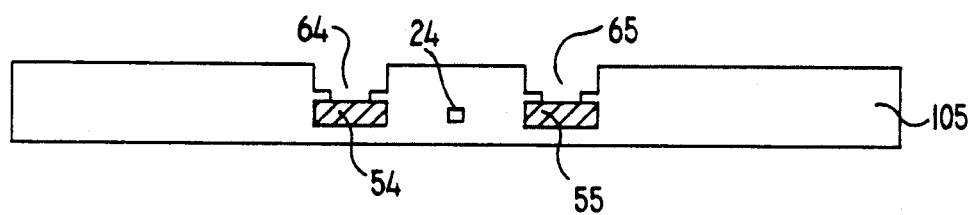
FIGS. 3A, B and C are series of cross-sectional views of the third embodiment shown in FIG. 2, taken along lines A—A, B—B, and CC, showing the capillary track and reagent stacks.
Figure 3B:
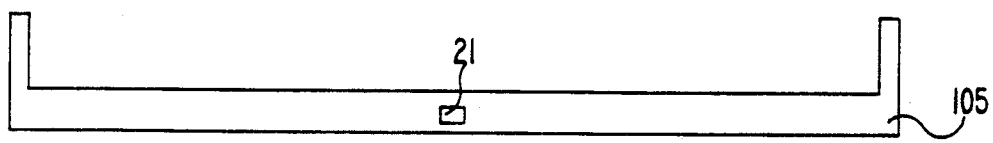
Figure 3A:
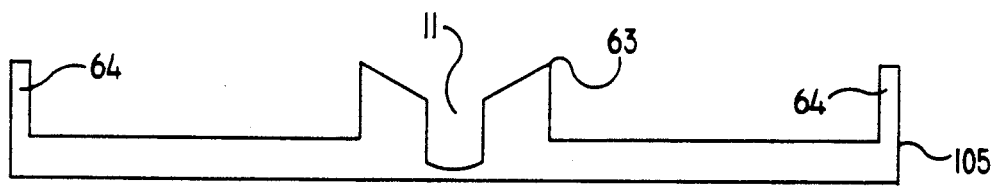

FIG. 3 shows a series of cross-sectional views taken through cartridge 105 as shown in FIG. 2 at locations A—A (panel A of FIG. 3), B—B (panel B), and C—C (panel C).

Panel A shows a cross-sectional view of cartridge 105 at application site 11. Application site 11 is seen to be a cavity formed in a raised surface of cartridge 105 surrounded by sloping surfaces and a lip 63 which acts to ensure that sample at the application site is directed into the cavity and thus to capillary passageway 21. The entire area surrounding application site 11 is surrounded by a further raised rim 64, which acts to retain sample near the application site in the event that sample is misapplied or when sample spills over lip 63, as discussed below.

Panel B shows a cross-sectional view further along the capillary passageway 21, and shows that capillary passageway 21 is formed in the interior of the housing that forms cartridge 105.

Panel C is a cross-sectional view taken along line C—C at the location of two of the four assay stacks. Assay stacks 54 and 55 are visible in this view along with intermediate capillary passageway 24 which is visible in the center of cartridge 105 as it leads in the direction of assay stacks 51 and 52 (which are not visible in this view). At the location of reaction stack 54 is an opening 64 which allows a reflectance reading to be made from the surface of the assay stack. A similar opening 65 is present for assay stack 55. Details of this opening, the assay stack, and capillary passageways leading to the assay stack are set forth in other Figures.

Figure 4:
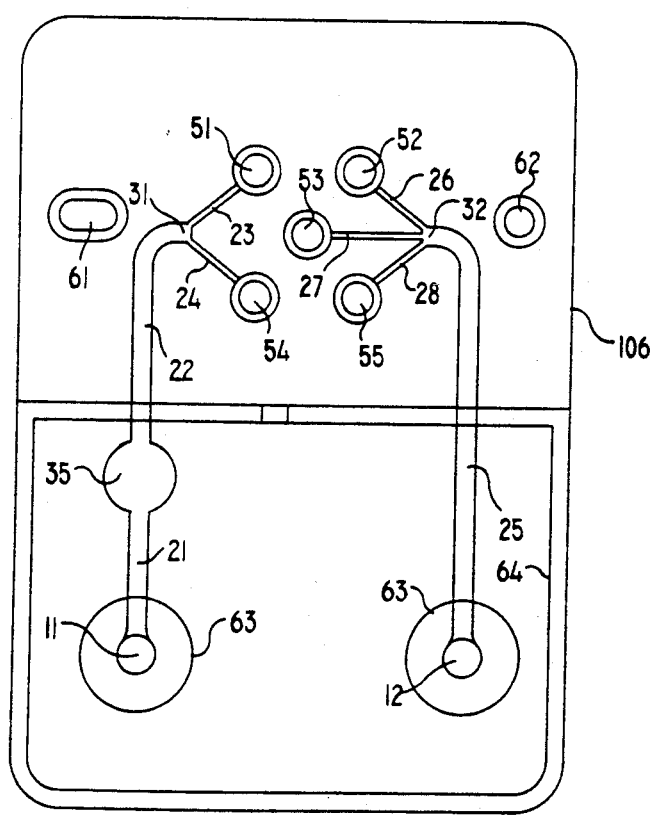
FIG. 4 is a plan view of a sixth embodiment of a cartridge of the invention.

FIG. 4 is a plan view of a further embodiment of the invention that would be a member of the same set of cartridges to which cartridge 105 of FIG. 3 belongs. Cartridge 106 of FIG. 4 and cartridge 105 of FIG. 2 are related to each other in the manner shown by cartridges 103 and 104 of FIG. 1. In other words, they have assay stack locations in common and the same outer dimensions so that they can be used interchangeably in a single monitor.

Cartridge 105 contains many of the same features of cartridge 105, such as the lip 63 surrounding application site 11 and the surrounding lip 64 protecting spills in the entire sample application area. Additionally, holes 61 and 62 are provided for locator pins to ensure proper registration of the cartridge in the monitor. This cartridge differs in having a second application site 12 with its surrounding lip 65. Additionally, a mixing chamber 35 is present after initial capillary passageway 21 to provide for any of the operations that would be desirable in a capillary cartridge, as have been described for previous cartridges. The operation of the various capillary passageways 22–28, branch points 31 and 32, and assay stacks 51–55 will evident from the similar features described in the previous embodiments.

All of the cartridges described here are intended for use with an unmeasured sample. Provided sufficient sample is applied, the same assay result will be provided by the monitor regardless of sample volume, provided that several control features are included in the cartridge.

Figure 5:
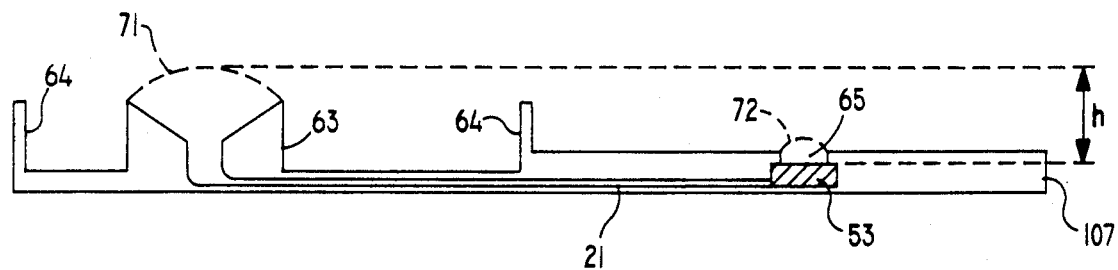
FIG. 5 is a cross-sectional view of a seventh embodiment of a cartridge showing forces that lead to continued flow of sample into an assay stack.

For example, when a large volume of sample is applied to the device, (i.e., greater than the minimum required to fill all the assay stacks), there is a tendency for sample fluid to continue to flow into the assay stacks as illustrated by the dashed line 72 showing the potential location of excess sample in FIG. 5. Gravity acts on the sample fluid column in capillary 21 when the upper surface 71 of the remaining sample is above the upper surface of sample fluid that has reached the top of the assay stack 53 (the potential energy difference results from gravity acting over height "h" in FIG. 5). Osmotic forces are also present (the assay stack contains osmotically active materials) so there is also a tendency for fluid to move into the stack in response to osmatic pressure. Surface tension forces when the sample is bowed above the top of the sample application site as shown at 71 in FIG. 5 also drive liquid into the assay stacks. The consequence of these forces is indicated by the dashed line 72 above the assay stack. Liquid from the sample tends to accumulate on top of the stack in the absence of appropriate fluid control features. thereby compromising reflectance measurements made from the optical surface at the top of the stack, which is ideally flat, and potentially contaminating the monitor with a bio-hazardous sample. This potential problem has been addressed by a set of fluid control elements that can be applied to any cartridge that uses an initial capillary passageway followed by a capillary reaction stack.

Figure 6:
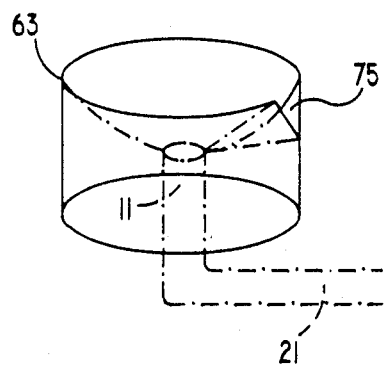
FIG. 6 is a perspective view of an application site with an overflow control slot.
Figure 7:
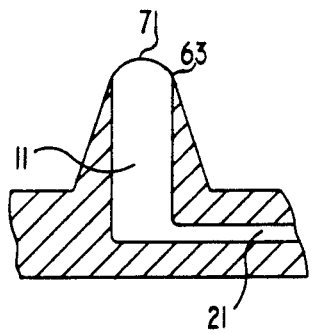
FIG. 7 is a cross-sectional view of a different embodiment of application site overflow control.

A first precaution is to design the sample application site to overflow when more than the maximum volume of sample has been applied. This is easily accomplished by providing a cut-out slot 75 in the upper region of the application site lip 63, as shown in FIG. 6 (in which dashed lines represent edges visible through the translucent plastic application region). This cut-out slot, which can be of any shape, also prevents formation of a sessile drop (i.e., drop 71 in FIG. 5). This feature limits the maximum extent of the excess-sample volume to a range that can be dealt with by the other control elements. Of course, other techniques can also be used to avoid accumulation of excess sample at the application site. The simplest technique is indicated in FIG. 7, in which the application site is not surrounded by a nearby downward-sloping surface intended to aid in application of sample to the application site, but by a sharp edge. In this case, the maximum volume of the application site is the maximum volume including the sessile drop shown by line 71. Although this represents a simple solution to excess sample, unfortunately application of sample to the site becomes more difficult, since a slightly misdirected sample may entirely miss application site 11.

Further control over sample volume is provided by carefully balancing the liquid-holding capacities of different parts of the cartridge. The capacity of the track connecting the sample application volume and the stacks can be selected to be just equal to, or preferably just slightly more than (by about 5 to 25%, preferably about 15%), the minimum volume required to fill the assay stack or stacks. In this way, much of the volume of sample is contained within the cartridge below the level of the top of the stack, so that the gravity pressure is minimized. For samples ranging in volume from the minimum sample size to the volume of the stacks plus the volume of the sample-transport capillaries, not only is the gravity force removed, but the capillary force becomes negative as the sample is drawn into the track. The stacks have very high capillary forces that can overcome the negative capillary force and gravity; the device therefore works properly even when remaining sample is drawn into the track, leaving the application site empty.

Figure 8:
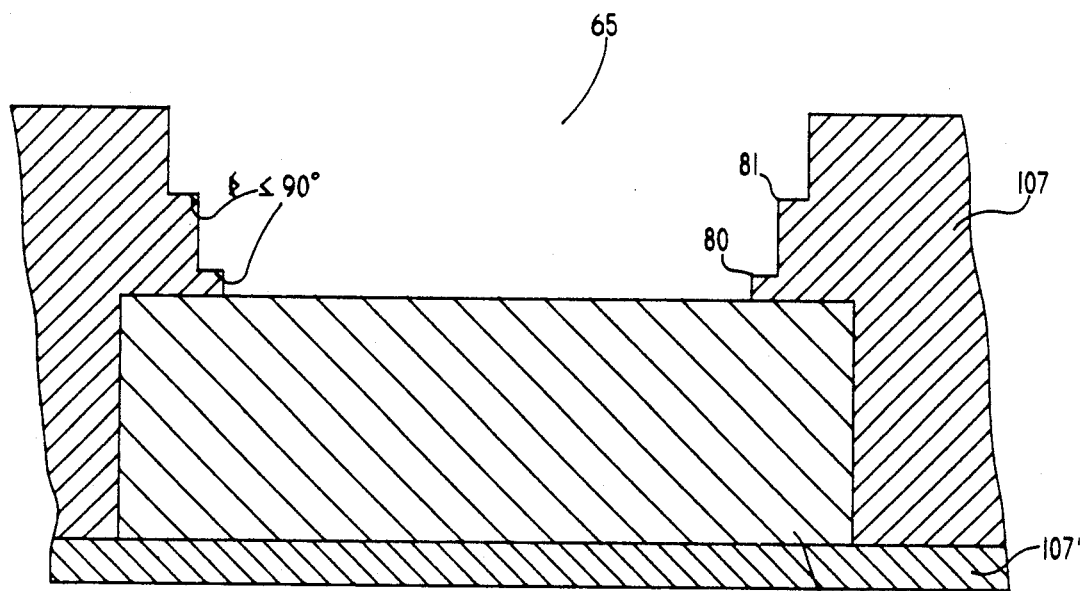
FIG. 8 is an expanded cross-sectional view of an optical window at an assay stack location showing use of ledges to prevent curvature of fluid surfaces.

A "ledge" can also be added to the stack cavity (FIG. 8) to minimize the volume of fluid that can accumulate on top of the stack. The edge of the ledge acts as a "stop-flow junction," which has been previously described for other operations in capillary cartridges. Two such ledges with appropriate edges 80 and 81 are visible in FIG. 8. These edges are sharply defined and generally have interior angles of 90° or less. By making the ledge thickness in the vertical direction small, the pooling can be significantly reduced. The volume between the top of the stack and the top surface of the cartridge is by necessity quite large to reduce the risk of contaminating the monitor with sample. The ledge effectively reduces this volume that otherwise could fill completely with fluid. The ledge also helps to keep the potentially hazardous sample from contaminating the monitor. As will be seen from the discussion below, this ledge, combined with other control features, allows even the small amount of liquid on the stack surface to be eventually drawn back into the stack.

Figure 9:
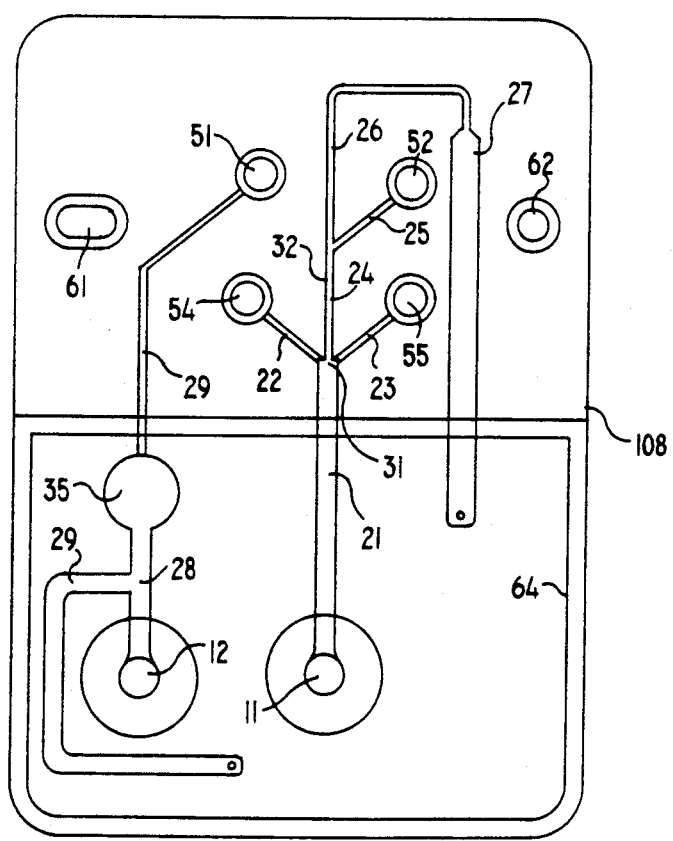
FIG. 9 is a plan view of a fourth embodiment of the invention showing capillary passageways used to control fluid flow and prevent improper operation of the cartridge.

Overflow/drain capillaries can also be added to the cartridge to actively prevent fluid accumulation above the stack. Two such capillaries are shown in FIG. 9. The drains are located and sized so that sample preferentially flows into the capillaries that feed the stacks and into the stacks until all the stacks are full. The capillary force in the drain capillaries is greater than the forces that promote pooling. This dual requirement is easily achieved by choice of appropriate dimensions, as discussed below. The volume of the drain capillaries is chosen to accommodate the largest possible sample volume (i.e., just enough to cause the application site to overflow). The drain capillaries will be better understood when considered with the other parts of cartridge 108.

The sample-transport capillary channels 21-25 and porous matrices for each assay 52, 54, and 55 together comprise a volume that is greater than the possible volume held in application well 11 from a single application of sample. In this way, there will be no excess sample in the application well when the assay is read, a condition that has been shown to cause variability in the saturation of the optical assay stacks with fluid. Capillary channel 21 itself leading from the application site to the assay sites has, in preferred embodiments, a volume slightly larger than the volume required to fill the assay sites 52, 54, and 55. The depths and widths of the capillary channels are designed to allow the entire sample applied in channel 21 to be drawn into the smaller capillary channels and assay sites beyond branch point 31. While sample flows to the sites, air drawn from the application site will displace the sample in channel 21, so that all of the sample can be utilized, making the assay efficient from the standpoint volume applied. This is possible because the motive capillary pressure supplied by the leading edge meniscus of the sample in the branching tracks beyond branch point 31 overcomes the opposing retarding capillary pressure of the initial track 21 supplied by the trail edge meniscus.

The capillary pressure, P, is a function of the two principal radii of curvature of the capillary channel R1 and R2 (assuming a rectangular channel):

$P = \sigma \cos \theta (1/R1 + 1/R2).$ where $\sigma$ is the surface tension of the sample and $\theta$ is the contact angle of the sample with the cartridge surface. Thus, even if the depths of the channels before and after branch point 31 are the same, the relatively narrow width of the channels beyond branch point 31 produce a higher motive capillary pressure relative to the retarding pressure in capillary 21. As an example, the dimensions of channel 21 can be 0.015" deep by 0.05 to 0.2" wide, whereas beyond branch point 31, the channels can be 0.015" deep by 0.02" wide.

If excess sample is applied to the application site 11, some of it will flow into the overflow track 26/27. The capacity of this track is such that any amount of sample applied in one application to application site 11 could be accommodated in the large overflow channel 26/27. Conversely, in the case where the minimum amount of sample is applied to application site 11 and some of it enters the overflow channel beyond branch point 32, capillary forces will eventually draw sample back into the main channel, as the capillary pressure of the overflow is less strong than that of either the branching tracks leading to the assay sites or the stacks. As an example, to achieve this balance, the channel beyond 32 can increase from 0.015" to 0.018" in depth, effectively reducing the capillary pressure.

In the track leading from application site 12 on the cartridge, a different strategy is followed for optimum results. In this assay, only a small volume of sample mixed with reagent from mixing chamber 35 is available to flow to assay stack 51. The inclusion of any overflow track after the mixing chamber 35 risks diverting some of this limited sample. For this special low-volume situation, an overflow channel 29 branches off the main channel 28 at branch point 33. As described above, the capillary pressure of the overflow 29 is designed to be weaker than the capillary pressure of channel 28 and mixing chamber 35. In this way, when a minimum amount of sample is applied to 12, any sample diverted to the overflow 29 will eventually be pulled back into the main channel by higher capillary pressures. However, if excess sample has been applied to 12, the channel 29 has the capacity to contain the maximum possible volume applied in one application, avoiding the possible oversaturation of assay site 51 by retention of excess sample at the application site and the resulting gravitational pressure.

The systems described above for control of sample volume can be readily summarized and understood by reference to the liquid-holding capacity of various parts of the cartridge. The cartridge is designed for application of a single drop of sample by a one-time operation that is as instantaneous as physically possible, such as by touching a drop of blood pendent from a finger (obtained by a capillary finger stick) to the application port. This application port, typically a cavity located in an exterior surface of the housing that forms the cartridge, will have an inherent liquid-holding capacity resulting from the size of the cavity. The cavity is typically present in the portion of the housing that extends above its surrounding area so that excess sample applied to the cavity will merely flow off the sides of this raised portion onto the surface of the cartridge, where it can be retained by a surrounding lip, as shown in the Figures described above. The capacity of the application site therefore refers to the amount of sample that will enter the application site when added as a single bolus, as described above. This will typically be almost equal to the physical volume of the application port itself since flow into capillary 21 will be slow relative to the sample application rate.

A second capacity that must be controlled is the capacity of the sample-transporting capillary passageway or passageways that are present in the housing connecting the sample application site to the reflectance reading site and its porous matrix. The capacity of this capillary passageway (here the singular is used to refer to all such passageways) is simply the volume of the passageway. When overflow capillaries are present, their capacities are included in the capacity of the sample-transport system for comparison to the volume of the application site, but they are not considered when comparing to the matrix capacity, since, as discussed above, the directly transporting capillaries fill in preference to the overflow capillaries. More detail on appropriate capillaries to include in capacity comparisons to is given below.

It should be noted that not all tracks of a given cartridge will have all preferred factors of the invention.

For example, the two tracks in cartridge 108 of FIG. 9 comprise different features of the invention.

Finally, the porous matrix itself in which a reflectance reading will be made will have an inherent internal capacity in its pores.

These different capacities are controlled so that in one preferred embodiment the sample-transport capacity is greater than the porous-matrix capacity. Thus, if a sample is smaller than that which is required to saturate the matrix (a condition which, if unrecognized, would lead to false assay results), the sample will entirely fill the sample-transport capacity before reaching the porous matrix. Such a system is present in the right-hand track of cartridge 108 or FIG. 9. Thus, by providing appropriate sizes and hydrophobic/hydrophilic character of the capillary passageway walls, capillary forces at the leading and following edges of the sample can be balanced, thereby preventing the sample from flowing into the matrix. These balanced forces are provided using standard techniques of capillary transport control, which typically involves controlling the radius of curvature for the leading and trailing sample meniscuses and the height of the sample at its two ends relative to each other. Meniscus curvature is readily accomplished by providing identical capillary cross-sectional dimensions at the locations where the leading and trailing edge of the sample will be found and by providing that the characteristics of the walls are the same at both locations. However, it is also possible to provide different cross-sectional dimensions while providing different surface energies at the two locations or different heights so that capillary forces remain in balance. It should be recalled that capillary forces are caused by surface tension effects at the leading and trailing edges, and that a chamber or passageway completely filled with liquid produces no capillary forces. Thus, when a sample leaves the application port (where it may be influenced by gravity with a portion of the liquid being higher than other portions) and enters a horizontal sample-transporting system, sample flow will cease if the trailing edge of the sample exerts a retarding force identical to the advancing capillary force at the leading edge of the sample regardless of the intervening structure of the capillary passageway.

Another volume relationship that is maintained in a different (or the same) preferred embodiment is the relationship of the application-site capacity to the sum of the sample-transport capacity (both direct and overflow) and the porous-matrix capacity. The application-site capacity needs to be less than the sum, so that when excess sample is applied to the application site, it will flow away as previously described and therefore not remain in the physically higher application site to provide gravitational pressure on the sample in the matrix.

As an extra safety measure for the assays and to protect the inside optical components of the monitor from contamination by the sample, the optical window design includes features to limit the rising of sample in the optical windows towards the optics, which can occur when the carrier membrane is full of plasma and there is excess sample still draining from the application site into the overflow areas (as might occur if a user accidentally applied sample again after the assay begins). The horizontal portions in the window break the upward force that normally pulls fluid up in a capillary. In this way, if excess fluid pools on the edges of the carrier membrane during flow of sample through the cartridge, this pooling is limited to a small volume, which is later quickly drained when all of the excess sample has been drained from the application site. These "stop-flow junctions" are discussed above in more detail.

Figure 10:
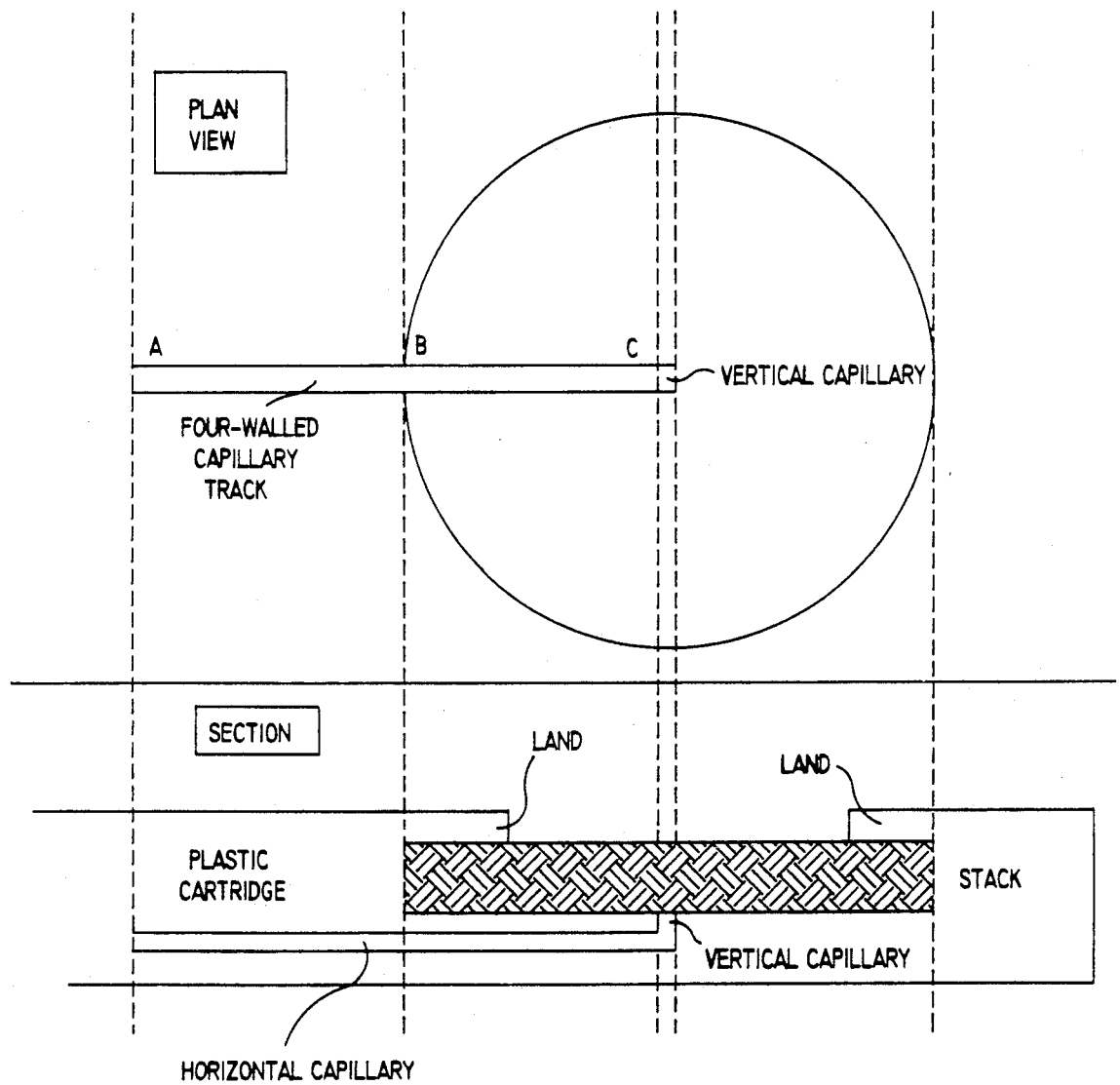

A number of other fluid control capillaries can be used to advantage with any of the embodiments of the present invention. For example, the embodiments of the Figures shown previously have a capillary in the interior of the housing that enters the space holding the assay stack at the edge of the assay stack. Thus, sample will enter the assay stack at one edge and spread through the assay stack horizontally as well as toward its upper surface where reflectance will be measured. Such side entry can result in uneven color formation on some reaction stacks, and more uniform entry of sample into the reaction stack is preferred. This can be accomplished in a number of ways. For example, a horizontal, 4-walled capillary track can lead beneath the assay stack to the center of the stack and be connected thereto by a small vertical capillary. Such an embodiment is shown in FIG. 10. Sample then enters the center of the assay stack and spreads uniformly over the whole assay stack.

However, using the fluid distribution scheme shown in FIG. 10 complicates production of the housing that forms the cartridge. The housing is generally prepared from two or more, preferably two, plastic pieces with the interior spaces being formed when the pieces are joined together. Because of the geometry required of the embodiment shown in FIG. 10, at least three pieces are required.

Figure 11:
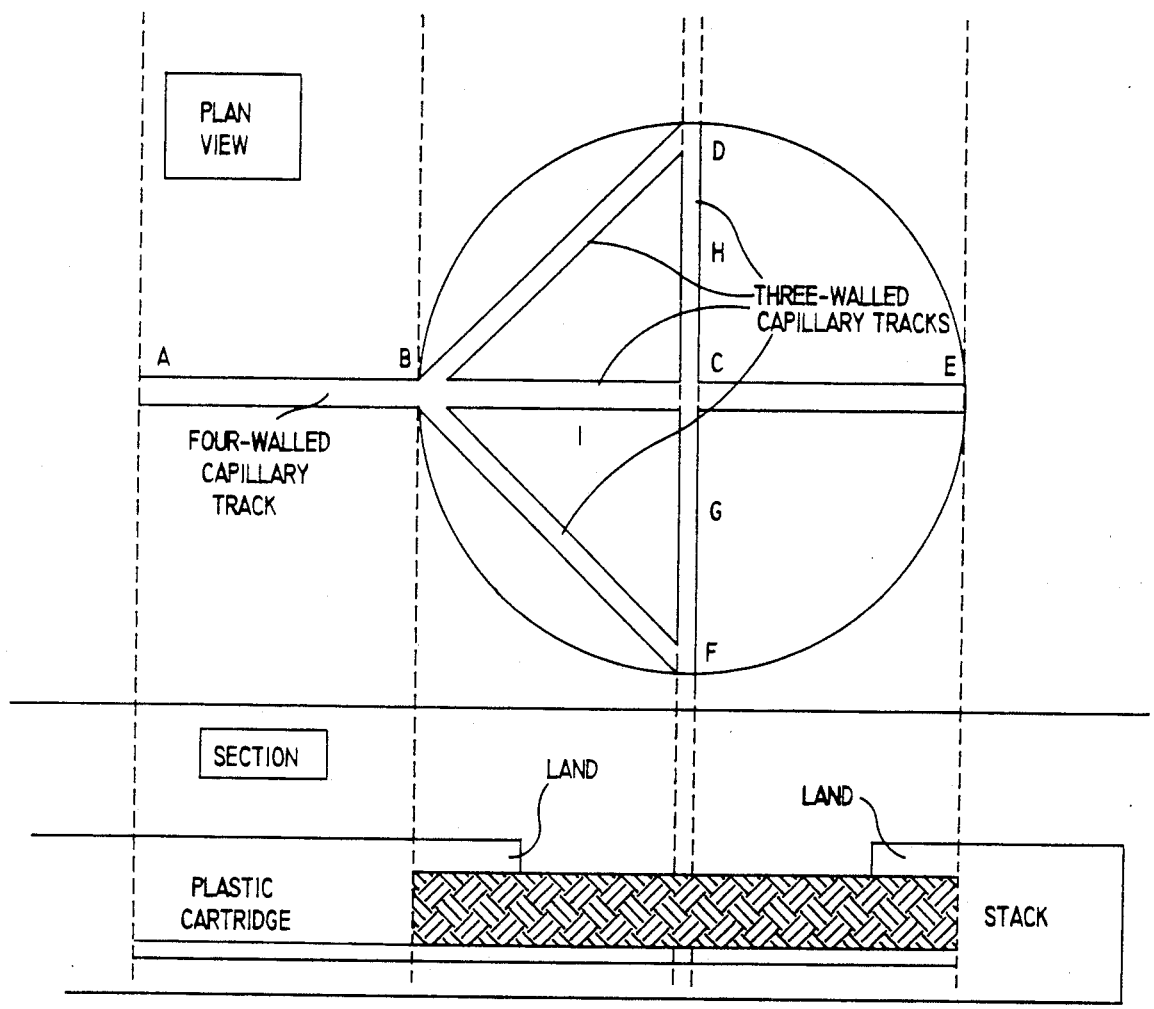

However, a cartridge formed from only two plastic cartridge parts can be prepared that provides satisfactory and substantially uniformed distribution of fluid into the assay stack. Such an embodiment is shown in FIG. 11, in which a 4-walled capillary track enters the space in which the assay stack will be located on the side much as before. However, the 4-walled capillary track is located just below the surface of the space that will contain the stack, and 3-walled capillary tracks (i.e., capillary spaces that are essentially grooves in the bottom surface of the area that will hold the assay stack) continue into the area beneath the assay stack. The bottom surface of the assay stack form the top surface (fourth wall) of these capillary tracks. Although a particular geometry is shown in FIG. 11, numerous other geometries of these grooves can be used to accomplish the same purpose; i.e., the distribution of fluid in capillary passageways beneath the capillary stack so that fluid enters the stack from all areas beneath the stack.

An alternative geometry that guides fluid to the center of the capillary stack as shown in in FIGS. 12 and 13. In FIG. 12, a typical sample-transport capillary 21 approaches the space beneath assay stack 53 and opening 65. Capillary 21 enters a wedge-like open space 41 beneath assay stack 53. At the bottom of space 41 is a small groove 42 which acts as a three-walled capillary channel in space 41. Groove 42 begins in the bottom of capillary channel 21 before channel 21 enters space 42. Panels A-E of FIG. 13, which are cross-sectional views taken along lines A—A through E—E of FIG. 12, shows the development of capillary groove 42 as views move from panel A to panel E. Additionally, the rising nature of the floor space 21 is illustrated in panels C-E. Capillary groove 42 acts to draw a sample entering space 41 upward along the bottom-sloping surface of space 41 so that sample contacts assay stack 53 at its center, thereby providing the desired uniformity of application. The capillary groove provides a strong force to draw sample toward the center of the matrix because of its small width. The space has a typical width of 0.020" and the groove is typically 0.005".

A further embodiment of the invention is shown in FIG. 14. The previously described cartridges have all shown assay stacks on the same surface as the application site. While this is generally true, it is also possible to provide an assay stack on the opposite side of the cartridge from the application site. Such an embodiment is shown in cartridge 109 of FIG. 14. Here application site 11 is located on a top surface of the cartridge, while capillary passageway 21 leads to assay stack 53 that is open to a reflectance reading through cavity 65 on the bottom surface of cartridge 109. By providing some assay locations on the top surface of the cartridge and other assay locations on the bottom surface of the cartridge, the optical systems present in the monitor used to measure reflectance readings can be separated from each other more readily so that more optical readings can be taken in the same limited amount of space.

The assay stacks used in a cartridge of the invention can vary widely depending on the specific assay being carried out. In some cases, a simple, porous, reflective matrix can be used when previous chambers in the capillary passageway leading to the assay stack carry out all operations necessary for determination of a result other than the reflectance reading itself. However, in most instances the assay stack will comprise a reflective matrix along with other elements designed to handle fluids. A typical assay stack can comprise as the first element in order of contact by a sample supplied through the capillary passageway, a porous, fluid-handling and transfer element that contains one or more reagents or that otherwise acts upon the sample, for example by filtering red blood cells from plasma. Sample then passes from this initial porous element to a matrix from which the reflectance reading will be made. Reagents required for a particular analysis can be located anywhere in the capillary track leading from the application site to the reflective matrix, up to and including the matrix itself. A number of different examples of assay stacks are set out in the examples that follow.

Additionally, it should be noted that the present invention is directed to the fluid handling system that directs sample to the very small assay stacks that are used in the present invention. Thus, any porous system designed to contain reagents and/or to be used to provide a reflectance reading can be used as an assay stack of the present invention. Numerous porous elements that provide for fluid handling in other manners are described in the patent and scientific literature. Small portions of such materials (such as could be prepared using a circular punch) can be cut out of numerous commercial preparations and inserted into a cartridge of the invention in order to utilize the fluid-handling characteristics of the cartridge. Thus, the present invention is not limited to any particular reaction stack or to any particular chemistry.

The invention now being generally described, the same will be better understood by reference to the following detailed examples, which are provided for illustration only and is not to be considered limiting of the invention unless so specified.

EXAMPLE

Example 1: Assay Cartridge

An assay cartridge was prepared from ABS Plastic substantially in the form as described in FIGS. 2 and 3. The cartridge had a width of 1.750" and a length of 2.500". Application site 11 had a capacity of 45 μl. Capillary 21 had a volume of 6.6 μl with track dimensions of 0.040" by 0.010" in cross-sectional area. Branch capillaries 22, 23, 25, and 26 each had a volume of 0.3 μl and cross-sectional areas of 0.010 by 0.010". Intermediate capillary 24 had a volume of 0.9 μl and a cross-sectional area of 0.020 by 0.010". The total matrix capacity was about 32–36 μl. In some cases, chemistry was optimized using a capillary track with a single application site, capillary track, and assay stack.

Example 2: Assay Stacks

Assay stacks have been optimized for a number of chemistries including hemoglobin assays. The assay stack for hemoglobin comprises 4 layers, numbered 1–4 in the order of blood contact. Layer 1 is a lysis disk made of ultra-high molecular weight polyethylene 0.031 inch thick and having 54% porosity with an average pore size of 25.5 micron. The material is commercially available from Porex Technologies. Layer 2 is a spreading layer made of nylon mesh 3-2F/186 having a thickness of 9 mil (Tetko). Layer 3 is designed to trap fragments of red blood cells produced by lysis in the lysing disk. This is a polyether sulfone assymeteric membrane available from Sartorius. The fourth layer, which is the reflectance reading matrix, is prepared from HT Tuffryn HT200, a polysulfone material prepared by Gelman Sciences. The lysing disk contains the only reagents in this system, namely a detergent that lyses the red blood cells (sodium deoxycholate and Theist) along with standard reagents for the measurement of hemoglobin. These reagents and their quantities are shown in Example 3.

Example 3: Hemoglobin assay chemistry used in assay stack

Theist and sodium deoxycholate, which are surfactants, can be incorporated into a porous Porex filter of a multilayered assay stack to rupture the membrane of red blood cells in the sample to release hemoglobin. Hemoglobin is then oxidized to methemoglobin (FeIII) and together with azide form stable axidemethemoglobin. Hemoglobin concentration is directly proportional to color intensity. These reactions are shown below.

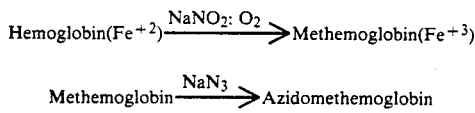

Table 1 shows the reagent concentrations and components used to prepare a hemoglobin assay stack for use in a cartridge of the invention.

TABLE 1

| Hemoglobin Test Composition, Reagent, Reagent Concentration Per Test, Vendor | | |
|---|---|---|
| Reagents | Quantity/Test[a] (mg) | Vendor |
| Theist | 1.836 | Boehringer Mannheim |
| Sodium Deoxycholate | 0.366 | Sigma Chemical Co. |
| Sodium Nitrite | 0.1829 | Sigma Chemical Co. |
| Sodium Azide | 0.0306 | Kodak Chemical Co. |
| Glucose | 0.3057 | Sigma Chemical Co. |
| UHMW | / | Porex Technologies |

TABLE 1-continued

Hemoglobin Test Composition. Reagent.
Reagent Concentration Per Test, Vendor

| Reagents | Quantity/Test[a] (mg) | Vendor |
|---|---|---|
| Polyethylene Nylon Mesh | / | Tetko Co. |
| HT200 Polysulfone | / | Gelman Sciences |

[a]Based on multilayered film technique using Porex as the lysing pad (pad size 32 mil thick and 136 mil diameter).

The indicated reagents were dissolved in degassed D.I. water and stirred overnight at ambient temperature. Porex sheet stock was lowered into degassed Bulk Reagent solution so that the Porex carrier was impregnated completely and uniformly. Excess reagent was blotted from the supporting mesh before transfer to a drying tunnel. Preliminary drying was achieved in a drying tunnel of controlled air flow at 40° C. for 4 hours. The reagent carriers were then subjected to a high vacuum for 12 hours. The resulting hemoglobin reagent carrier was stored in a dark drying containment at 4° C.

The reagent carrier disk was used as layer 1 to prepare a reagent stack for hemoglobin by layering with the previously described stack layers 2-4 (see Example 2). The resulting reagent stack was inserted into a cartridge prepared as described above in Example 1. Dose/response and clinical evaluations were carried out on the assay of the invention (Biotrack assay) and compared to the commercially available Hemocue ™ assay for hemoglobin using samples of whole blood. Results, which are shown in Tables 2 and 3, demonstrate that the cartridge of the invention is capable of producing useful clinical information while providing the advantages of the invention previously described.

TABLE 2

Hemoglobin Test Dose/Response

| Analyte (g/dL) | K/S |
|---|---|
| 5 | 0.3 |
| 10 | 0.7 |
| 15 | 1.1 |
| 20 | 1.4 |
| 25 | 1.7 |

TABLE 3

Clinical Correlation for Hemoglobin
Test Compared With Reference Method

| | Hb (g/dL) | |
|---|---|---|
| Sample | Hemocue | Biotrack |
| 1 | 2.8 | 3.2 |
| 2 | 5.0 | 5.3 |
| 3 | 7.2 | 7.2 |
| 4 | 10.1 | 10.2 |
| 5 | 13.9 | 12.2 |
| 6 | 13.9 | 14.8 |
| 7 | 16.4 | 17.2 |
| 8 | 18.6 | 17.2 |
| 9 | 18.4 | 18.9 |
| 10 | 19.6 | 19.0 |

Example 4: Demonstration of red cell filtration

In an experiment to determine the effectiveness of the filter, prototype 4-window cartridges and monitors were used. Cartridges contained stacks comprised of antibody impregnated-polypropylene filters, Gelman TR-3000 membrane and two layers of ST-69 (Schleicher and Schuell). No assay chemistry was present in the stacks. Blood (45% hematocrit), the corresponding plasma, and serum samples with known levels of hemolysis were applied to the cartridges in the usual way and K/S values recorded after 3 min. at 585 nm. To evaluate the effects red cells that were not removed by the filter blood containing known, samples with low hematocrits were applied directly to the optical surface of the stack.

The results given below in Table 4 show that >99% of the red cells were removed and that <1% hemolysis occurred.

TABLE 4

| Sample K/S serum | Hematocrit % | Hemolysis[1] % | K/S- |
|---|---|---|---|
| Plasma | 0 | 0.0 | 0.000 |
| Blood | 45 | 0.0 | 0.056 |
| Serum | 0 | 1.0 | 0.113 |
| Serum | 0 | 2.0 | 0.171 |
| Serum | 0 | 5.0 | 0.343 |
| Blood | 1.3 | 0.0 | 0.172 |
| Blood | 2.5 | 0.0 | 0.370 |
| Blood | 5.0 | 0.0 | 0.776 |

[1]Given as hematocrit equivalent

Example 5: Multi-analyte Assay System: Glucose, Cholesterol, and Hemoglobin Determinations The layout of capillary tracks and stacks in multi-analyte assay cartridges is essentially equivalent to the cartridge shown in FIGS. 2 and 3. All four stack cavities were filled with stacks which were of up to three different types. A plan view of the prototype cartridge is shown in FIG. 2. A sectional view of the assay stack is given in FIG. 3. The filter in the glucose and cholesterol stacks is a non-woven polypropylene felt (Ergon 5.7 oz/sq. yrd.) impregnated with antibody to red cells (Orgenon-Teknika, 1 mg/mL) then dried. The filter stacks also contain a membrane and a mesh to control fluid movement. In all cases, at the top of the stack there is a porous membrane that serves as the reflective member. In the case of the glucose and cholesterol stacks the assay reagent is incorporated into this membrane. The hemoglobin stack has detergent impregnated into a porous plastic disc. Stack configurations are given in Table 5.

TABLE 5

| Component | Assay | | |
|---|---|---|---|
| | Glucose | Cholesterol | Hemoglobin |
| A | HT-Tuffryn 450 (Gelman) | HT-Tuffryn 650 (Gelman) | HT-Tuffryn 200 (Gelman) |
| B | Nylon mesh (Tetko, 6 mil) | Nylon mesh (Tetko, 6 mil) | Asymmetric membrane (Sartorius, 6 mil) |
| C | 0.22μ Membrane (Millipore GVWP) | 0.22μ Membrane (Millipore GVWP) | Nylon mesh (Tetko, 9 mil) |
| D | Polypropylene felt | Polypropylene felt | UMHW Polyethylene (Porex, 25.5 micron) |

Before assembly, the plastic parts of the cartridge were subjected to plasma etching which reduces the contact angle between blood and plastic and so promotes capillary flow in the cartridge. Cartridges were assembled after punching discs of each element that are inserted into the upper part of the cartridge. The lower part of the cartridge is then welded to the upper to capture the stacks in the stack cavities and seal the capillary channels. Cartridges were individually pouched in aluminum/plastic foil with a desiccant pack.

Compositions of the assay chemistry are given below in terms of quantity per test:

Glucose: Glucose oxidase (*Aspergillus niger*) (1.4 IU), Horse-radish peroxidase (0.28 IU), 4-aminoantipyrene (22 micrograms), N-ethyl-N-(2-hydroxy-3-sulphopropyl)-3,5-dimethoxyaniline (44 micrograms).

Cholesterol: Cholesterol esterase (Pseudomonas) (2.8 IU), cholesterol oxidase (*Streptomyces cinnamomeus*) (0.36 IU), Horse-radish sulphopropyl)-3,5-dimethoxyaniline (0.44 mg).

Hemoglobin: Thesit TM (1.8 mg), sodium deoxycholate (0.37 mg), sodium nitrite (0.18 mg) and sodium azide (31 micrograms).

Aqueous compositions of the above formulated with buffers, stabilizing reagents and detergents were impregnated into the appropriate stack material and dried.

In the glucose and cholesterol stacks, red cells are removed by passable through a filter prior to moving into a "carrier" membrane which contains assay chemistry. Since some of the chemistries (glucose and cholesterol) require oxygen, the cartridge provides access to the atmosphere at the top surface of the assay stack.

Calibrators were blood samples supplemented with analyte or diluted analyte-free plasma as needed.

Assay protocols: After insertion of the cartridge into the monitor, blood samples (typically 35 uL) were added to the sample application site. Reactions were generally followed for three minutes and reflectance values recorded after three minutes or when there was no change in reflectance with time. Usually, reflectance was measured at a single wavelength (585 nm) for all assays. Analyte concentrations in clinical samples and control materials were determined using the Kodak DT-60 for glucose and cholesterol and the Hemocue TM for hemoglobin.

Calculation of results: Relative reflectance, R was usually defined as the ratio of signal after completion of the reaction to that recorded prior to wetting of the stack. A simplified version of the Kubelka-Munk relations $K/S = (1 - R)^2 / 2R$ was used to calculate K/S where K is the absorption coefficient of the chromophore/membrane pair which is a function of the absorbance and concentration of the chromophore and S is the scattering coefficient of the membrane. For optically thick membranes, K/S is directly proportional to the concentration of colored product. K/S values were converted to analyte concentrations with a calibration function (usually a four-term polynomial) derived from data from at least five calibration materials spanning the assay range.

RESULTS

Cartridge Performance

The cartridge serves to deliver blood to the assay stacks to filter red cells in the cholesterol and glucose stacks and to mix sample and reagents. Good reproducibility of flow time from sample application site to stack and time to saturate the assay stack was found. The time from sample application to completion of the wetting of the optical surface ranged from 45 to 90 seconds for blood of 20 to 60% hematocrit respectively.

The efficiency of the red cell filter was evaluated in glucose assay stacks omitting assay reagent and measuring the color of the optical membrane at 585 nm corresponding to a major absorbance of hemoglobin. Any leaked red cells or hemolysis would be detected in this way. Less than 1% leakage or hemolysis would be detected in this way. Less than 1% leakage or hemolysis was found. The filter works by agglutination of the red cells and depth filtration of the agglutinated cells in the fibrous mesh of the filter. The filter is effective for blood up to 60% hematocrit.

Dissolution and mixing of reagents and sample occurs spontaneously as the sample fluid moves into the reagent-impregnated porous media. The reproducibility of this process is good, as shown by the assay precision (see later).

For each assay, the color yield corresponding to the assay quantitation range was determined both theoretically and by direct experiment. Yields were approximately 80% for the glucose and cholesterol assays and 100% for hemoglobin. For candidate membranes, S values were measured. By inspection of the results it was then possible to choose a membrane/chromophore pair that gives a range of K/S values closes to the optimum range of 0.2-2.0. This optimum range was calculated by applying error analysis. The error functions exhibit shallow minima in the K/S range 0.2-2.

The assay chemistries selected use high concentrations of enzymes and excess enzyme substrates for rapid and complete conversion of analyte to the measured reaction product. A typical assay time course shows that about 20 seconds after sample application reflectance begins to decline. Prior to this decline the monitor determines stack reflectance and compares it with pre-established norms to verify that the cartridge is not defective. There is a rapid decline in reflectance as the optical membrane wets. This is due to the increase in refractive index of medium impregnating the membrane pores: air being replaced by plasma. This change causes reduction of the specific reflectance (S) of the membrane. The reagents dissolve rapidly in the plasma and react with the analyte. Within typically two to three minutes, the reaction is complete as shown by the lack of change of reflectance. Independent measurements of the chemical yield of product from analyte show that at least 80% conversion occurs in all the assays over the entire analyte range. Assays in which there is complete conversion to colored product and where the reflective matrix is optically thick should have a linear response of K/S to analyte. This is indeed the case for all three assays: glucose, cholesterol and hemoglobin. The response is essentially linear up to the highest analyte levels. At high analyte levels the response declines somewhat due to incomplete conversion. Such non-linearity is of course, easily dealt with by appropriate calibration.

After calibration, all the assays (glucose, cholesterol and hemoglobin) gave results that correlate well with established methods for patient samples. The glucose assay correlates excellently with a commercially available method, and produces results that overall agree absolutely (regression line slope is 1.0 and intercept is negligibly small). Correlation statistics for all the assays produced a correlation coefficient of 0.99. For these correlation studies it was convenient to use heparinized venous blood samples. To compare finger-stick and venous samples results in the system paired tests were performed. Results were analyzed by Wilcoxon signed rank paired statistics. For all the assays (glucose, cholesterol and hemoglobin), using 20 paired samples the p value was about 0.9 for 95% confidence indicating that finger-stick and venous results were equivalent.

Precision of the assays at this state of development, using cartridges assembled by a semi-automated process, range from 3-6% CV in the middle of the quantitated range for all the analytes.

Interference in assays due to common problematic factors have been evaluated. Bilirubin up to 600 mg/dL. Lipemia up to 12 g triglyceride/L and hemolysis up to 10 g/L have no significant impact on assay results.

Hemolysis can occur due to inappropriate handling of the specimen. A simple algorithm constructed from the known spectral properties of the reaction product and of hemoglobin permits the calculation of both chromogen and hemoglobin concentrations from data collected at 585 nm (where the reaction product and hemoglobin both absorb strongly and 637 nm (where the reaction product absorbs and hemoglobin has little absorption). Hemoglobin concentrations less than those at which there is interference in the glucose and cholesterol assays are easily measured. Hemolyzed samples that would give incorrect assay results can be identified in this way.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

We claim:

1. An analytical cartridge, comprising:
   a. a liquid impervious housing,
   b. a sample application site comprising a cavity located in an exterior surface of said housing and having an application-site liquid-holding capacity,
   c. a reflectance reading site comprising a chamber in said housing,
   d. means for venting said chamber to atmosphere,
   e. a sample-transporting capillary passageway in said housing connecting said sample application site to said reflectance reading site and having a sample-transport liquid-holding capacity, and
   f. a porous matrix located in said reflectance reading site and having a porous-matrix liquid-holding capacity,
wherein said sample-transport capacity is greater than said porous-matrix capacity and said application-site capacity is less than the sum of said sample-transport capacity and said porous-matrix capacity.

2. The analytical cartridge of claim 1, wherein said sample-transporting capillary passageway comprises wall means for subjecting said sample to equal motive and retarding forces at locations of leading and trailing meniscuses when a sample having a volume equal to said porous-matrix capacity enters said capillary passageway from said application site, whereby said sample is prevented from flowing into said matrix, the locations of said leading and trailing meniscuses for said volume of sample equal to said matrix capacity being identified as a leading equal-volume location and a trailing equal-volume location, respectively.

3. The analytical cartridge of claim 2, wherein said capillary passageway and said application site are connected at an application-site junction and said capillary passageway comprises wall means for providing a radius of curvature at said junction for a trailing sample meniscus located at said junction equal to a radius of curvature for a leading sample meniscus located at said leading equal-volume location.

4. The analytical cartridge of claim 2, wherein said capillary passageway has equal cross-sectional dimensions at said equal-volume locations.

5. The analytical cartridge of claim 2, wherein said capillary passageway has different cross-sectional dimensions at said equal-volume locations, but said equal forces are provided by walls of said capillary having different surface energies or gravitational potentials at said equal-volume locations.

6. The analytical cartridge of claim 1, wherein said cartridge comprises directing means for causing sample applied near said application site to flow into said application site.

7. The analytical cartridge of claim 6, wherein said directing means comprises a surface substantially surrounding said application site and sloping toward said application site.

8. The analytical cartridge of claim 6, wherein said directing means further comprises means for excluding sample in excess of said application-site capacity from said application site.

9. The analytical cartridge of claim 8, wherein said directing means site comprises a surface substantially surrounding said application and sloping toward said application site and said means for excluding sample comprises a slot in an upper region of said surface.

10. The analytical cartridge of claim 2, wherein said cartridge further comprises an overflow capillary passageway connected to said sample-transporting capillary passageway at an overflow junction.

11. The analytical cartridge of claim 10, wherein said overflow junction is located in said sample-transporting capillary passageway beyond said leading equal-volume location.

12. The analytical cartridge of claim 11, wherein said overflow capillary passageway comprises wall means for forming a meniscus that exerts a capillary force less than that present in said sample-transporting capillary passageway or said porous matrix when a sample is present in said overflow caapillary passageway and in said sample-transporting capillary passageway or porous matrix.

13. The analytical cartridge of claim 10, wherein said overflow junction is located in said sample-transporting capillary passageway before said leading equal-volume location.

14. The analytical cartridge of claim 13, wherein said overflow capillary passageway comprises wall means for forming a meniscus that exerts a capillary force less than that present in said sample-transporting capillary passageway when a sample is present in said overflow caapillary passageway and in said sample-transporting capillary passageway.

15. The analytical cartridge of claim 1, wherein (1) said cartidge comprises multiple reflectance reading sites containing multiple reflectance-reading matrices, said muliple matrices jointly having said porous-matrix capacity, and (2) said sample-transporting capillary passageway comprises (a) branch capillaries leading to each of said sites from one or more branch sites in said sample-transporting capillary passageway and (b) an initial trunk capillary connecting said sample application site to a first branch site of said branch sites in said sample-transporting capillary passageway.

16. The analytical cartridge of claim 15, wherein said trunk capillary has a trunk liquid-holding capacity larger than said porous-matrix capacity.

17. The analytical cartridge of claim 16, wherein said branch capillaries each have wall means for providing a motive capillary force larger than retarding capillary force in said trunk capillary when a sample is present in said sample-transport capillary and said sample has a leading meniscus in one of said branch capillaries and a trailing meniscus in said trunk capillary.

18. The analytical cartridge of claim 17, wherein said trunk capillary comprises wall means for subjecting said sample to equal motive and retarding forces at locations of leading and trailing meniscuses when a sample having a volume equal to said porous-matrix capacity enters said truck capillary from said application site, whereby said sample is prevented from flowing into said branch capillaries, the locations of said leading and trailing meniscuses for said volume of sample equal to said matrix capacity being identified as a leading equal-volume location and a trailing equal-volume location, respectively.

19. The analytical cartridge of claim 1, wherein said means for venting comprises an opening in an upper surface of said housing at said chamber, whereby a surface of said reflectance matrix is exposed to external irradiation and reflectance through said opening.

20. The analytical cartridge of claim 19, wherein said opening comprises a stop-flow junction below said upper surface.

21. The analytical cartridge of claim 20, wherein said opening is circular and said stop-flow junction comprises a ledge having an edge with an interior angle of 90° or less projecting into said opening.

22. A diagnosis system, which comprises:
   a. a monitor, comprising:
      i. means for detecting multiple reflectance readings in an array of individual locations,
      ii. means for registering an analytical cartridge at a fixed location and orientation relative to said array in an interior space of said monitor, and
      iii. means for determining and displaying analytical results from reflectance readings obtained at individual locations in said array; and
   b. a first analytical cartridge, comprising:
      i. a liquid impervious housing,
      ii. a sample application site in said housing at a location that is outside said monitor when said cartridge is registered in said monitor by said means for registering,
      iii. one or more reflectance reading sites positioned in said housing to register with one or more of said locations in said array when said cartridge is registered in said monitor,
      iv. a capillary pathway in said housing leading from said sample application site to each of said one or more reflectance reading sites, and
      v. a reflectance matrix located in at least one of said reflectance reading sites.

23. The system of claim 22, wherein multiple reflectance reading sites are present in said cartridge.

24. The system of claim 23, wherein said system further comprises a second analytical cartridge capable of measuring at least one analyte not in common with analytes measured by said first cartridge.

25. The system of claim 24, wherein said second analytical cartridge comprises at least one reflectance reading site at a location in said array different from reflectance reading sites utilized by said first analytical cartridge.

26. The system of claim 22, wherein said monitor further comprises means for detecting and identifying said analytical cartridge when inserted into said monitor and said cartridge further comprises information encoded on said cartridge whereby said means for detecting and identifying said analytical cartridge identifies said cartridge as belonging to a predetermined cartridge type recognized by said monitor when said cartridge is inserted in said monitor.

27. The system of claim 26, wherein said second analytical cartridge comprises at least one capillary passageway different from capillary passageways utilized by said first analytical cartridge.

28. The system of claim 22, wherein said housing comprises a capillary tree connecting a single application site to a plurality of assay stacks, wherein said capillary tree comprises an initial capillary passageway with a first cross-sectional area and a plurality of branch capillary passageways connecting said initial capillary passageway to said assay stacks, either directly or through further branch capillary passageways, wherein each of said branch capillaries in a pathway connecting said trunk capillary to one of said assay stacks is smaller than said trunk capillary and any preceding branch capillary in said connection.

29. The system of claim 22, wherein said reflectance reading sites are present in an array accessible on one flat surface of said housing.

30. An analytical cartridge, comprising:
   a. a liquid impervious housing,
   b. a sample application site comprising a cavity located in an exterior surface of said housing.
   c. a reflectance reading site comprising a chamber in said housing,
   d. a sample-transporting capillary passageway in said housing connecting said sample application site to said reflectance reading site,
   e. a porous matrix located in said reflectance reading site, and
   f. an opening in said housing at said chamber, whereby a surface of said reflectance matrix is exposed to potential external irradiation and reflectance through said opening, comprises a stop-flow junction.

31. The analytical cartridge of claim 30, wherein said opening is circular and said stop-flow junction comprises a ledge having an edge with an interior angle of 90° or less.

32. The analytical cartridge of claim 31, wherein said opening is circular and said stop-flow junction occurs at junction in said opening where said opening changes from a proximal smaller diameter to a distal larger diameter, proximal and distal locations in said opening being relative to said surface of said reflectance matrix.

33. In a diagnostic cartridge comprising a four-walled interior capillary passageway that supplies an analytical liquid to a chamber containing a porous, disk-shaped matrix having a diameter D greater than its height and a bottom surface substantially in contact with the floor of said chamber, an improvement which comprises:
   said four-walled capillary passageway located so that it enters said chamber at a lower edge of said disk, one or more three-walled capillary passageways provided in said floor connected to the entrance location of said four-wall capillary passageway into said chamber, wherein no point on the bottom surface of said disk is further than one-half D from at least one point of said three-walled capillary passageways.

34. The cartridge of claim 33, wherein said four-walled capillary passageway enters an empty space beneath said floor, said space having a secondary floor that slopes upward to a central location of said matrix and a three-walled capillary channel is present in said secondary floor, whereby sample entering said space is drawn upward by said three-walled capillary channel to said matrix.

* * * * *